US009238796B2

(12) United States Patent
Yoshida et al.

(10) Patent No.: US 9,238,796 B2
(45) Date of Patent: Jan. 19, 2016

(54) CELL GROWTH-PROMOTING PEPTIDE AND USE THEREOF

(71) Applicant: TOAGOSEI CO., LTD., Tokyo (JP)

(72) Inventors: Tetsuhiko Yoshida, Tsukuba (JP); Nahoko Kobayashi, Tsukuba (JP)

(73) Assignee: TOAGOSEI CO. LTD., Tokyo (JP)

( * ) Notice: Subject to any disclaimer, the term of this patent is extended or adjusted under 35 U.S.C. 154(b) by 0 days.

(21) Appl. No.: 14/341,177

(22) Filed: Jul. 25, 2014

(65) Prior Publication Data

US 2014/0335613 A1 Nov. 13, 2014

Related U.S. Application Data

(63) Continuation-in-part of application No. 13/701,747, filed as application No. PCT/JP2011/062809 on Jun. 3, 2011, now Pat. No. 8,822,408.

(30) Foreign Application Priority Data

Jun. 4, 2010 (JP) ................................. 2010-128648

(51) Int. Cl.
*A61K 38/02* (2006.01)
*A61K 38/18* (2006.01)
*C12N 5/02* (2006.01)
*C12N 5/0775* (2010.01)
*C07K 14/47* (2006.01)

(52) U.S. Cl.
CPC .......... *C12N 5/0663* (2013.01); *C07K 14/4711* (2013.01); *C07K 2319/74* (2013.01); *C12N 2501/998* (2013.01)

(58) Field of Classification Search
CPC ........... C12N 2501/998; C12N 5/0663; C07K 14/435; C07K 2319/74; C07K 14/4711
See application file for complete search history.

(56) References Cited

U.S. PATENT DOCUMENTS

| | | | |
|---|---|---|---|
| 4,578,269 A | 3/1986 | Morein | |
| 4,744,983 A | 5/1988 | Morein | |
| 4,867,975 A | 9/1989 | Gelb, Jr. | |
| 4,981,684 A | 1/1991 | MacKenzie et al. | |
| 5,178,860 A | 1/1993 | MacKenzie et al. | |
| 5,242,932 A | 9/1993 | Gandy et al. | |
| 5,441,931 A | 8/1995 | Sprecher et al. | |
| 5,519,003 A | 5/1996 | Mochly-Rosen et al. | |
| 5,679,355 A | 10/1997 | Alexander et al. | |
| 5,961,970 A | 10/1999 | Lowell et al. | |
| 6,037,521 A | 3/2000 | Sato et al. | |
| 6,333,167 B1 | 12/2001 | Quinet et al. | |
| 6,340,583 B1 | 1/2002 | Yan et al. | |
| 6,403,353 B1 | 6/2002 | Yan et al. | |
| 6,423,684 B1 | 7/2002 | Mochly-Rosen et al. | |
| 6,476,189 B1 | 11/2002 | Yamakawa et al. | |
| 2003/0125242 A1 | 7/2003 | Rosenecker et al. | |
| 2003/0166215 A1 | 9/2003 | Yan et al. | |
| 2003/0229202 A1 | 12/2003 | Guo et al. | |
| 2004/0175751 A1 | 9/2004 | Yan et al. | |
| 2004/0186052 A1 | 9/2004 | Iyer et al. | |
| 2004/0226056 A1 | 11/2004 | Roch et al. | |
| 2005/0129701 A1 | 6/2005 | Marasco et al. | |
| 2006/0057668 A1 | 3/2006 | Yoshida et al. | |
| 2006/0100134 A1 | 5/2006 | Guo et al. | |
| 2006/0166917 A1 | 7/2006 | Lindeman et al. | |
| 2006/0270834 A1 | 11/2006 | Kanno | |
| 2007/0065941 A1 | 3/2007 | Kondo et al. | |
| 2008/0076145 A1 | 3/2008 | Cummings et al. | |
| 2009/0004144 A1 | 1/2009 | Tabira et al. | |
| 2009/0253618 A1 | 10/2009 | Kanno et al. | |
| 2010/0074925 A1 | 3/2010 | Carmon | |
| 2010/0093059 A1 | 4/2010 | Wolff et al. | |
| 2010/0169988 A1 | 7/2010 | Kohli et al. | |
| 2010/0209490 A1 | 8/2010 | Morita et al. | |
| 2010/0297758 A1 | 11/2010 | Yoshida et al. | |
| 2011/0229912 A1 | 9/2011 | Cai et al. | |
| 2011/0269942 A1 | 11/2011 | Morita et al. | |
| 2012/0035112 A1 | 2/2012 | Yoshida et al. | |
| 2012/0122210 A1 | 5/2012 | Yoshida et al. | |
| 2012/0122225 A1 | 5/2012 | Kobayashi et al. | |
| 2012/0208752 A1 | 8/2012 | Yoshida et al. | |
| 2013/0005034 A1 | 1/2013 | Yoshida et al. | |
| 2013/0079273 A1 | 3/2013 | Yoshida et al. | |
| 2013/0345408 A1 | 12/2013 | Fukushima at at. | |

(Continued)

FOREIGN PATENT DOCUMENTS

| EP | 0 653 154 A2 | 5/1995 |
|---|---|---|
| EP | 1 634 956 A1 | 3/2006 |

(Continued)

OTHER PUBLICATIONS

Dec. 18, 2014 Notification of Reasons for Refusal issued in Japanese Application No. 2011-538478.
Cells-Merck Manual, from http://www.merckmanuals.com/home/fundamentals/the_human_body/cells.html, pp. 1-2, accessed Dec. 24, 2014.
DNA and cell division, from http://www.bbc.co.uk/schools/gcsebitesize/science/add_aqa/inheritance/dna_cell_division . . . , pp. 1-6, accessed Dec. 28, 2014.
O'Sullivan et al., "Cytokine Receptor Signaling Through the Jak-Stat-Socs Pathway in Disease," Molecular Immunology, vol. 44, pp. 2497-2506, 2007.
Stem cell information, from http://stemcells.nih.gov/StaticResources/info/popups/glossary.html, pp. 1-6, accessed Dec. 23, 2014.
Woodbury et al., "Adult Rat and Human Bone Marrow Stromal Cells Differentiate Into Neurons," Journal of Neuroscience Research, vol. 61, pp. 364-370, 2000.

(Continued)

*Primary Examiner* — Julie Ha
*Assistant Examiner* — Li Ni Komatsu
(74) *Attorney, Agent, or Firm* — Oliff PLC

(57) ABSTRACT

The pharmaceutical composition provided by the present invention comprises at least one pharmaceutically acceptable carrier, and an active ingredient including an artificially synthesized peptide comprises: (A) an amino acid sequence constituting a cell-penetrating peptide and (B) an amino acid sequence constituting the signal peptide in amyloid precursor protein (APP) or an N-terminal partial amino acid sequence or C-terminal partial amino acid sequence from the amino acid sequence constituting that signal peptide.

4 Claims, No Drawings

(56) References Cited

U.S. PATENT DOCUMENTS

| | | | |
|---|---|---|---|
| 2014/0072592 A1 | 3/2014 | Okamoto et al. | |
| 2014/0178990 A1 | 6/2014 | Yoshida et al. | |
| 2015/0126434 A1 | 5/2015 | Kobayashi et al. | |
| 2015/0273018 A1 | 10/2015 | Kobayashi et al. | |

FOREIGN PATENT DOCUMENTS

| | | | |
|---|---|---|---|
| EP | 1 918 297 A1 | 5/2008 | |
| JP | A-7-132033 | 5/1995 | |
| JP | A-9-323928 | 12/1997 | |
| JP | 2000063400 A | 2/2000 | |
| JP | 2001186887 A | 7/2001 | |
| JP | A-2001-199997 | 7/2001 | |
| JP | A-2003-137899 | 5/2003 | |
| JP | A-2004-357543 | 12/2004 | |
| JP | 2005-511047 A | 4/2005 | |
| JP | A-2005-154338 | 6/2005 | |
| JP | A-2005-330206 | 12/2005 | |
| JP | B2-3854995 | 12/2006 | |
| JP | 2007-517057 A | 6/2007 | |
| JP | A-2007-145761 | 6/2007 | |
| JP | A-2007-159429 | 6/2007 | |
| JP | A-2009-209064 | 9/2009 | |
| JP | A-2011-16763 | 1/2011 | |
| JP | 2012-518042 A | 8/2012 | |
| WO | WO 95/21252 A2 | 8/1995 | |
| WO | WO 02/18572 A2 | 3/2002 | |
| WO | WO 02/077171 A2 | 10/2002 | |
| WO | 03/048337 A2 | 6/2003 | |
| WO | WO 03/076561 A2 | 9/2003 | |
| WO | 03091429 A1 | 11/2003 | |
| WO | WO 2004/056854 A1 | 7/2004 | |
| WO | WO 2005/086800 A2 | 9/2005 | |
| WO | 2006/125360 A1 | 10/2006 | |
| WO | WO 2007/010989 A1 | 1/2007 | |
| WO | WO 2007/149293 A2 | 12/2007 | |
| WO | WO 2008/008569 A2 | 1/2008 | |
| WO | 2006/035350 A1 | 3/2008 | |
| WO | WO 2008/027017 A1 | 3/2008 | |
| WO | 2009/020093 A1 | 2/2009 | |
| WO | 2009/020094 A1 | 2/2009 | |
| WO | 2009/047002 A2 | 4/2009 | |
| WO | 2009/053696 A1 | 4/2009 | |
| WO | WO 2009/093692 A1 | 7/2009 | |
| WO | 2010/096470 A2 | 8/2010 | |
| WO | WO 2010/117078 A1 | 10/2010 | |
| WO | WO 2010/117079 A1 | 10/2010 | |
| WO | WO 2011/052679 A1 | 5/2011 | |
| WO | 2011152524 A1 | 12/2011 | |
| WO | 2012093706 A1 | 7/2012 | |
| WO | 2012093732 A1 | 7/2012 | |

OTHER PUBLICATIONS

Jan. 23, 2015 Office Action issued in U.S. Appl. No. 14/163,371.
Emmott et al., "Nucleolar targeting: the hub of the matter," *EMBO reports*, 2009, vol. 10, No. 3, pp. 231-238.
Goyal et al., "Phosphorylation-dependent Regulation of Unique Nuclear and Nucleolar Localization Signals of LIM Kinase 2 in Endothelial Cells," *Journal of Biological Chemistry*, 2006, vol. 281, No. 35, pp. 25223-25230.
Martoglio et al., "Signal sequences: more than just greasy peptides," *trends in Cell Biology*, 1998, vol. 8, pp. 410-415.
International Search Report issued in International Patent Application No. PCT/JP2011/062809 mailed Jul. 19, 2011.
International Preliminary Report on Patentability issued in International Patent Application No.PCT/JP2011/062809 dated Jan. 8, 2013.
Berendsen, "A Glimpse of the Holy Grail?," Science, vol. 282, No. 5389, pp. 642-643, Oct. 23, 1998.
Bochkov et al., "Phylogenetic Analysis of Partial S1 and N Gene Sequences of Infections Bronchitis Virus Isolates from Italy Revealed Genetic Diversity and Recombination," Virus Genes, vol. 35, pp. 65-71, 2007.
Boursnell et al., "Sequences of the Nucleocapsid Genes from Two Strains of Avian Infectious Bronchitis Virus," J. Gen. Virol., vol. 66, pp. 573-580, 1985.
Bradley et al., "Limits of Cooperativity in a Structurally Modular Protein: Response of the Notch Ankyrin Domain to Analogous Alanine Substitutions in Each Repeat," J Mol. Biol, vol. 324, pp. 373-386, 2002.
Cserpán et al., "The Mechanism of Nuclear Transport of Natural or Artificial Transport Substrates in Digitonin-Permeabilized Cells," Journal of Cell Science, vol. 108, pp. 1849-1861, 1995.
Eiges et al., "Establishment of Human Embryonic Stem Cell-Transfected Clones Carrying a Marker for Undifferentiated Cells," Current Biology, vol. 11, pp. 514-518, 2001.
Fang et al., "Selection of and Recombination between Minor Variants Lead to the Adaptation of an Avian Coronavirus to Primate Cells," Biochemical and Biophysical Research Communications, vol. 336, pp. 417-423, 2005.
Futaki et al., "Intracellular Protein Delivery Using Membrane-Permeable Peptides," Seibutsu to Kagaku, vol. 43, No. 10, pp. 649-653, 2005, with English-language translation.
Hilton et al., "Twenty Proteins Containg a C-Terminal SOCS Box Form Five Structural Classes," Proc. Natl. Acad. Sci. USA, vol. 95, pp. 114-119, Jan. 1998.
Kamura et al., "The Elongin BC Complex Interacts with the Conserved SOCS-Box Motif Present in Members of the SOCS, Ras, WD-40 Repeat, and Ankyrin Repeat Families," Genes & Development, vol. 12, pp. 3872-3881, 1998.
Kamura et al., "VHL-Box and SOCS-Box Domains Determine Binding Specificity for Cu12-Rbx1 and Cu15-Rbx2 Modules of Ubiquitin Ligases," Genes & Development, vol. 18, pp. 3055-3065, 2004.
Kang et al., "The Precursor of Alzheimer's Disease Amyloid A4 Protein Resembles a Cell-Surface Receptor," Nature, vol. 325, pp. 733-736, Feb. 19, 1987.
Kile et al., "The Suppressors of Cytokine Signalling (SOCS)," Cellular and Molecular Life Sciences, vol. 58, pp. 1627-1635, 2001.
Kobayashi et al., "Nucleolar Localization Signals of LIM Kinase 2 Function as a Cell-Penetrating Peptide," Protein & Peptide Letters, vol. 17, pp. 1480-1488, 2010.
Kwak et al., "Amyloid Precursor Protein Regulates Differentiation of Human Neural Stem Cells," Stem Cells Dev., vol. 15, No. 3, pp. 381-389, 2006.
Liu et al., "Rack 1 Competes with HSP90 for Binding to HIF-1$\alpha$ and is Required for $O_2$-Independent and HSP90 Inhibitor-Induced Degradation of HIF-1$\alpha$," Molecular Cell, vol. 25, pp. 207-217, Jan. 26, 2007.
Liu et al., "Calcineurin Promotes Hypoxia-Inducible Factor 1$\alpha$ Expression by Dephosphorylating RACK1 and Blocking Rack 1 Dimerization," Journal of Biological Chemistry, vol. 282, No. 51, pp. 37064-37073, Dec. 21, 2007.
Liu et al., "Rack1 vs. HSP90: Competition for HIF-1$\alpha$ Degradation vs. Stablization," Cell Cycle, vol. 6, No. 6, pp. 656-659, Mar. 15, 2007.
Marutle et al., "Modulation of Human Neural Stem Cell Differentiation in Alzheimer (APP23) Transgenic Mice by Phenserine," Proc. Natl. Acad. USA, vol. 104, No. 30, pp. 12506-12511, Jul. 24, 2007.
NCBI database Accession No. Q1M2X0, p. 1, accessed Nov. 7, 2012.
Ngo et al., "Computational Complexity, Protein Structure Prediction, and the Levinthal Paradox," *The Protein Folding Problem and Tertiary Structure Prediction*, K. Merz Jr. and S. Le Grand, Eds. pp. 491-494, Birchhuser Bosino 1994.
Pokorska et al., "The Analysis of the Transcriptional Activator PrnA Reveals a Tripartite Nuclear Localisation Sequence," J. Mil. Biol., vol. 298, pp. 585-596, 2000.
Reed et al., "Delineation and Modelling of a Nucleolar Retention Signal in the Coronavirus Nucleocapsid Protein," Traffic, vol. 7, pp. 833-848, 2006.
Rudinger, "Peptide Hormones," JA Parsons, Ed., pp. 1-7, Jun. 1976.
"Designing Custom Peptides," www.sigma-genosys.com/peptide_design.asp; Sigma-Genosys, pp. 1-2, accessed Dec. 16, 2004.
Sugaya et al., "Practical Issues in Stem Cell Therapy for Alzheimer's Disease," Curr. Alzheimer Res., vol. 4, No. 4, pp. 370-377, 2007 (Abstract Only).

(56) References Cited

OTHER PUBLICATIONS

Takei et al., "Possible Involvement of a Pertussis Toxin-Sensitive GTP-Binding Protein in Protein Transport into Nuclei Isolated from Rat Liver," J. Biochem., vol. 115, pp. 578-583, 1994.
Voet et al., "Biochemistry," John Wiley & Sons, Inc., pp. 235-241, 1995.
Yu et al., "Selective Assembly of HIV-1 Vif-Cul5-ElonginB-ElonginC E3 Ubiquitin Ligase Complex through a Novel SOCS Box and Upstream Cysteines," Genes & Development, vol. 18, pp. 2867-2872, 2004.
Mar. 1, 2011 European Search Report issued in European Application No. 09 704 366.5.
Dec. 5, 2011 European Office Action issued in European Application No. 09 704 366.5.
Apr. 7, 2009 International Search Report issued in International Application No. PCT/2009/051082.
Jul. 13, 2010 International Search Report issued in International Application No. PCT/JP2010/056510 (with translation).
Oct. 5, 2010 International Search Report issued in International Patent Application No. PCT/JP2010/062691 (with translation).
Oct. 5, 2010 International Search Report issued in International Patent Application No. PCT/JP2010/062693 (with translation).
Jan. 18, 2011 International Search Report issued in International Patent Application No. PCT/JP2010/069165.
Jun. 12, 2012 International Preliminary Report on Patentability and Written Opinion issued in International Patent Application No. PCT/JP2010/069165.
Mar. 29, 2010 International Preliminary Report on Patentability and Written Opinion issued in International Application No. PCT/JP2009/051082.
Aug. 17, 2011 Office Action issued in U.S. Appl. No. 12/864,147.
Sep. 30, 2011 Office Action issued in U.S. Appl. No. 12/864,147.
Mar. 12, 2012 Office Action issued in U.S. Appl. No. 12/864,147.
Nov. 14, 2012 Office Action issued in U.S. Appl. No. 13/386,539.
Nov. 14, 2012 Office Action issued in U.S. Appl. No. 13/386,582.
Jan. 31, 2013 Office Action issued in U.S. Appl. No. 13/258,788.
Feb. 22, 2013 Office Action issued in U.S. Appl. No. 13/386,539.
Feb. 22, 2013 Office Action issued in U.S. Appl. No. 13/386,582.
Apr. 17, 2013 Office Action issued in U.S. Appl. No. 13/503,220.
Alexander et al., "The Role of Suppressors of Cytokine Signaling (SOCS) Proteins in Regulation of the Immune Response," Annu. Rev. Immunol., vol. 22, pp. 503-529, 2004.
Larsen et al., "Suppressors of Cytokine Signalling: SOCS," APMIS, vol. 110, pp. 833-844, 2002.
Jun. 18, 2013 Supplementary European Search Report issued in European Application No. 10 82 6811.
Dieterlen-Lievre, "On the Origin of Haemopoietic Stem Cells in the Avian Embryo: An Experimental Approach," J. Embryol. exp. Morph., vol. 33, No. 3, pp. 607-619, 1975.
Aug. 7, 2013 Office Action issued in U.S. Appl. No. 13/258,788.
Aug. 6, 2013 Office Action issued in U.S. Appl. No. 13/386,582.
Copani et al., "Mitotic Signaling by β-amyloid Causes Neuronal Death," The FASEB Journal, vol. 13, pp. 2225-2234, Dec. 1999.
De Strooper et al., "Proteolytic Processing and Cell Biological Functions of the Amyloid Precursor Protein," Journal of Cell Science, vol. 113, pp. 1857-1870, 2000.
Zhang et al., "NSA2, A Novel Nucleolus Protein Regulates Cell Proliferation and Cell Cycle," Biochemical and Biophysical Research Communications, vol. 391, pp. 651-658, 2010.
Mar. 24, 2014 Office Action issued in European Application No. 10 826 811.1.
Apr. 22, 2014 Supplementary European Search Report issued in European Application No. 11 78 9925.2.
Neer et al., "The Ancient Regulatory-Protein Family of WD-Repeat Proteins," Nature, vol. 371, pp. 297-300, 1994.
Apr. 15, 2014 European Search Report issued in European Application No. 14153135.0.
Selkoe, "Normal and Abnormal Biology of the Beta-Amyloid Precursor Protein," Annu. Rev. Neurosci., vol. 17, pp. 489-517, 1994.
Hayashi et al., "Alzheimer Amyloid Protein Precursor Enhances Proliferation of Neural Stem Cells from Fetal Rat Brain," Biochemical and Biophysical Research Communications, vol. 205, No. 1, pp. 936-943, 1994.
Venkataramani et al., "Histone Deacetylase Inhibitor Valproic Acid Inhibits Cancer Cell Proliferation via Down-Regulation of the Alzheimer Amyloid Precursor Protein," The Journal of Biological Chemistry, vol. 285, No. 14, pp. 10678-10689, Apr. 2, 2010.
Kwak, "Studies on the Novel Function of Amyloid Precursor Protein in Glial Differentiation of Neural Stem Cells," Dissertation, pp. 1-173, 2006.
Jun. 25, 2013 Search Report issued in International Application No. PCT/JP2013/064393.
Soscia, Stephanie et al. "The Alzheimer's Disease-Associated Amyloid b-Protein Is an Antimicrobial Peptide". vol. 5, 1-10, 2010. PLoS ONE.
Papareddy, Praveen et al., "Antimicrobial activity of peptides derived from human b-amyloid precursor protein". vol. 18, 183-191, 2012, Journal of Peptide Science.
Panegyres, Peter et al. "The Function of the Amyloid Precursor Protein Gene and Its Derivative Peptides: I Molecular Biology and Metabolic Processing". vol. 2, 120-131, 2011, Neuroscience & Medicine.
Dec. 2, 2014 International Preliminary Report on Patentability issued in International Application No. PCT/JP2013/064393.
McKinnon et al., "Neurinflammation in Glaucoma," XIX Biennial Meeting of the International Society for Eye Research, Jul. 18-23, 2010, Montreal, Canada.
Luo at al., "Differential Functions of Tumor Necrosis Factor Receptor 1 and 2 Signaling in Ischemia-Mediated Arteriogenesis and Angiogenesis," The American Journal of Pathology, pp. 1886-1898, vol. 169, No. 5, Nov. 2006.
Nakazawa et al., "Tumor Necrosis Factor-? Mediates Photoreceptor Death in a Rodent model of Retinal Detachment," Investigative Opthamology & Visual Science, pp. 1384-1391, vol. 52, No. 3, Mar. 2011.
Clark at al., "Is TNF a Link between Aging-Related Reproductive Endocrine Dyscrasia and Alzheimer's Disease?" Journal of Alzheimer's Disease, pp. 691-699, vol. 27, 2011.
Sim et al., "Ligand-Dependent Activation of the Chimeric Tumor Necrosis Factor Receptor-Amyloid Precursor Protein (APP) Reveals Increased APP Processing and Suppressed Neuronal Differentiation," Neurosignals, pp. 9-23, vol. 18, 2010.
Nov. 12, 2013 International Search Report issued in International Application No. PCT/JP2013/078222.
Apr. 21, 2015 International Preliminary Report on Patentability issued in International Application No. PCT/JP2013/078222.
Paliga at al., "Human Amyloid Precursor-like Protein 1 cDNA Cloning, Ectopic Expression in COS-7 Cells and Identification of Soluble Forms in the Cerebrospinal Fluid," Eur. J. Biochem., vol. 250, pp. 354-363, 1997.
Lichtenthaler et al., "A Novel Substrate for Analyzing Alzheimer's Disease g-Secretase," FEBS Letters, vol. 453, pp. 288-292, 1999.
Rohn et al., "A Monoclonal Antibody to Amyloid Precursor Protein Induces Neuronal Apoptosis," Journal of Neurochemistry, vol. 74, pp. 2331-2342, 2000.
Kohler et al., "Continuous Cultures of Fused Cells Secreting Antibody of Predefined Specificity," Nature, vol. 256, pp. 495-497, Aug. 7, 1995.
Henderson at al., "HLA-A2.1-Associated Peptides from a Mutant Cell Line: A Second Pathway of Antigen Presentation," Science, 1992, vol. 255, pp. 1264-1266.
Hage et al., "Preprocalcitonin Signal Peptide Generates a Cytotoxic T Lymphocyte-Defined Tumor Epitope Processed by a Proteasome-Independent Pathway," PNAS, Jul. 2008, vol. 105, No. 29, pp. 10119-10124.
Abbott, "The Plaque Plan," Nature, Nov. 2008, vol. 456, pp. 161-164.
Nikolaev et al., "APP Binds DR6 to Trigger Axon Pruning and Neuron Death via Distinct Caspases," Nature, Feb. 2009, vol. 457, pp. 981-989.
Mar. 13, 2012 International Search Report issued in International Patent Application No. PCT/JP2012/050210.

(56) References Cited

OTHER PUBLICATIONS

Jul. 10, 2013 International Preliminary Report on Patentability issued in International Patent Application No. PCT/JP2012/050210.
Harlow at al., Antibodies; A Laboratory Manual, Spring Harbor Laboratory, 1988, Chapter 5, pp. 72-77.
Hopp at al., "Prediction of Protein Antigenic Determinants from Amino Acid Sequences," Proc. Natl. Acad. Sci. Usa, 1981, vol. 78, No. 6, pp. 3824-3828.
Water, from http://www.biology-online.org/dictionary/VVater, pp. 1-3, accessed Apr. 24, 2014.
DMSO—The Source Natural Foods, from http://thesourcenaturai.com/...isplayMonograph.asp?storelD=dhap6v4fb7sr2nm700akhlbd3cmfbxmid&DocID=bottorrline-dimethylsulfoxide, pp. 1-7, accessed Sep. 23, 2015.
Hilton et al., "Anti-Peptide Antibody Blocks Peptide Binding to MHC Class I Molecules in the Endoplasmic Reticulum", Journal of Immunology, vol. 166, pp. 3952-3956, 2001.
Pomroy et al., "Solubilization of Hydrophobic Peptides by Reversible Cysteine PEGylation", Biochemical and Biophysical Research Communications, vol. 245, No. 2, pp. 618-621, 1998.
Boulant et al., "Hepatitis C Virus Core Protein is a Dimeric Alpha-Helical Protein Exhibiting Membrane Protein Features", Journal of Virology, vol. 79, No. 17, pp. 11353-11365, 2005.
Extended European Search Report for European Patent Application No. 12731948.1, mailed Jul. 14, 2015.
Slivka et al., "Peptide Probes for Protein Transmembrane Domains" ACS Chem. Biol. 3(7):402-411, 2008.
Almen et al., "Mapping the Human Membrane Proteorne: A Majority of the Human Membrane Proteins can be Classified According to Function and Evolutionary Origin" BMC Biology 7:50, 2009 (14 pages).
Tam, "Synthetic Peptide Vaccin Design: Synthesis and Properties of a High-Density Multiple Antigenic Peptide System" Proc. Nat!. Acad. Sci. USA 85:5409-5413, 1988.
Beck et al., "Nucleotide Sequence of the Gene ompA Coding the Outer Membrane Protein 11 of *Escherichia coli* K-12" Nucleic Acids Research 8(13):3011-3027, 1980.
Miraglia et al., "A Novel Five-Transmembrane Hematopoletic Stem Cell Antigen: Isolation, Characterization, and Molecular Cloning" Blood 90(12):5013-5021, 1997.
International Search Report for PCT/JP2012/050136, mailed Feb. 28, 2012.
International Preliminary Report on Patentability for PCT/JP2012/050136, mailed Jul. 18, 2013.
Jul. 22, 2015 Office Action issued in U.S. Appl. No. 14/397,920.
Oct. 27, 2015 Office Action issued in U.S. Appl. No. 14/397,920.
Nov. 12, 2015 Office Action Issued in U.S. Appl. No. 13/978,419.
Apr. 23, 2015 Office Action issued in U.S. Appl. No. 13/978,584.
Sep. 3, 2015 Office Action issued in U.S. Appl. No. 13/978,584.
Aug. 14, 2015 Office Action issued in U.S. Appl. No. 13/978,419.

CELL GROWTH-PROMOTING PEPTIDE AND USE THEREOF

CROSS-REFERENCE TO RELATED APPLICATIONS

This application is a Continuation-in-Part of application Ser. No. 13/701,747 filed on Dec. 3, 2012, which issued as U.S. Pat. No. 8,822,408, which is a Section 371 National Phase of PCT International application No. PCT/JP2011/062809, the entire contents of both of which are hereby incorporated herein by reference. This application also claims priority right based on Japanese Patent Application No. 2010-128648 filed on Jun. 4, 2010, which is hereby incorporated by reference.

TECHNICAL FIELD

The present invention relates to a peptide capable of promoting proliferation of stem and other cells; and use thereof. Especially, it relates to a cell growth promoter (a composition) containing the peptide and a method to produce cells of interest at an increased growth rate using the peptide.

BACKGROUND ART

In the field of regenerative medicine, it has been a challenge to establish a method to proliferate cells of interest at a higher rate. In the fields of cell engineering and fermentation engineering, in order to increase the yield of the cells of interest themselves or to increase the efficiency of the cells (or tissue) of interest to produce products, it is desired to proliferate more efficiently the subject cultured cells (or cells constituting cultured tissue).

Conventionally, for the above purposes, various cell growth factors have been used. One example among the most frequently used growth factors is basic fibroblast growth factor (hereinafter, it may be referred to as "bFGF"). bFGF is known as a substance to exhibit an effect of promoting proliferation of various mesodermal and neuroectodermal cells in addition to fibroblasts and is a growth factor that is frequently used in promoting proliferation of various kinds of subject cells.

However, as the currently available bFGF is very expensive, it is financially difficult to use the growth factor in a relatively large quantity for cell proliferation. Moreover, using bFGF for the purpose of cell proliferation may become a significant cause to increase the cost of cell manufacturing and tissue regeneration involving the said proliferation.

Under these circumstances, research and development of a low-cost, mass-producible substance that has cell growth-promoting capability to replace the expensive cell growth factors such as bFGF are underway so far. For example, Patent Documents 1 to 3 listed below respectively describe a peptide that possesses cell growth-promoting capability and the respective Patent Literatures describe that by using the peptide, the growth rate of the test cells was increased.

CITATION LIST

Patent Literature

Patent Literature 1: Japanese Patent Application No. 2003-137899
Patent Literature 2: Japanese Patent Application No. 2005-154338
Patent Literature 3: Japanese Patent Application No. 2009-209064

Non Patent Literature

Non-Patent Literature 1: *EMBO Reports*, Vol. 10, No. 3, pp. 231-238 (2009)
Non-Patent Literature 2: *The Journal of Biological Chemistry*, Vol. 281, No. 35, pp. 25223-25230 (2006)
Non-Patent Literature 3: *Trends in Cell Biology*, Vol. 8, pp. 410-415 (1998)

SUMMARY OF INVENTION

An objective of the present invention is to provide a peptide having a composition that is different from those of the conventional cell growth-promoting peptides described in Patent Documents 1 to 3, the peptide being an artificial peptide that can exhibit a cell growth-promoting effect equal to or greater than bFGF. A further objective is to provide a cell growth promoter (pharmaceutical composition) containing such a peptide as an active ingredient. An additional object of the present invention is to provide a method of producing a specific desired cell using this peptide.

The cell growth promoter provided by this invention is characterized by that it comprises, as an active ingredient (i.e. a substance involved in promoting cell proliferation), at least one type of the peptide disclosed herein that possesses cell growth-promoting capability (hereinafter, it may be referred to as "peptide with cell growth-promoting capability").

In other words, the peptide according to this invention, which can be used as an active ingredient of the cell growth promoter, is an artificially synthesized peptide comprising in its peptide chain, partial amino acid sequences as specified in the following (A) and (B) respectively:

(A) an amino acid sequence constituting a cell-penetrating peptide, and (B) an amino acid sequence constituting the signal peptide in amyloid precursor protein (APP), or an N-terminal partial amino acid sequence that is a portion of the amino acid sequence constituting this signal peptide and that comprises at least five consecutive amino acid residues counting from the N-terminal amino acid residue of that sequence, or a C-terminal partial amino acid sequence that is a portion of the amino acid sequence constituting this signal peptide and that comprises at least five consecutive amino acid residues counting from the C-terminal amino acid residue of that sequence.

The cell growth promoter disclosed herein contains at least one pharmaceutically acceptable carrier (for example, at least one substrate to contribute to increase the stability of the peptide, or a fluid medium such as physiological saline or various buffers).

The present inventors have come to accomplish this invention by finding out that a cell growth-promoting activity that matches or exceeds that of bFGF can be exhibited by a synthetic peptide constructed using an amino acid sequence that constitutes a portion of a polypeptide heretofore known for functionalities completely unrelated to cell growth.

Thus, the synthetic peptide that is the base component of the cell growth promoter disclosed herein has the amino acid sequence of a cell-penetrating peptide as the amino acid sequence specified for (A); and has, as the amino acid sequence specified for (B), all or a portion of the amino acid sequence constituting the signal peptide of amyloid precursor protein (wherein a portion refers to a partial sequence from the N-terminal side or C-terminal side of this signal peptide).

Because the cell growth promoter disclosed herein comprises, as an active ingredient, a peptide that can be readily produced by an artificial method such as chemical synthesis (or biosynthesis), it can be used (typically as a substitute for bFGF) to promote proliferation of eukaryotic cells of interest without using an expensive cell growth factor such as bFGF or the like in a large quantity. Since it is possible to reduce the use of an expensive cell growth factor like bFGF or others, a cost reduction can be achieved in cell culturing or biologically active substance production that involves cell proliferation; or the cost increase can be suppressed.

The present inventors carried out detailed investigations of the properties of the amyloid precursor protein and focused on its signal peptide. The amyloid precursor protein may also be regarded, so to speak, as a substance from which Alzheimer's disease starts in accordance with the amyloid hypothesis, according to which the amyloid precursor protein (APP) in the neurons of the brain is cleaved by β-secretase and γ-secretase, typically with the production of amyloid β-protein composed of 40 or 42 amino acid residues, and neurons are destroyed by the aggregation (accumulation) of this amyloid β (particularly Aβ$_{42}$) in the brain, resulting in the onset of Alzheimer's disease.

It was discovered that a high growth-promoting effect for various cultured cells (eukaryotic cells) is exhibited by a synthetic peptide fabricated so as to contain all or a portion of the amino acid sequence constituting the signal peptide in the amyloid precursor protein. The present invention was based on this discovery.

In the present specification, "APP signal peptide-related sequence" is used as a collective term for amino acid sequences that constitute the signal peptide in the amyloid precursor protein (APP) and for partial amino acid sequences present in this signal peptide (i.e., partial amino acid sequences at its N-terminal side and partial amino acid sequences at its C-terminal side). In addition, for the amino acid sequences described in this specification, the left side is always the N-terminal side and the right side is always the C-terminal side.

In a preferred aspect of the cell growth promoter disclosed herein, the signal peptide of the amyloid precursor protein is composed of the following amino acid sequence:

(SEQ ID NO: 19)
M L P G L A L L L L A A W T A R A or (SEQ ID NO: 20)
M L P S L A L L L L A A W T V R A.

In addition, the artificially synthesized peptide has, as the amino acid sequence specified by (B), the amino acid sequence represented by SEQ ID NO: 19 or SEQ ID NO: 20, or an N-terminal partial amino acid sequence that is a portion of the amino acid sequence represented by SEQ ID NO: 19 or SEQ ID NO: 20 and that comprises at least five consecutive amino acid residues counting from the N-terminal amino acid residue of that sequence, or a C-terminal partial amino acid sequence that is a portion of the amino acid sequence represented by SEQ ID NO: 19 or SEQ ID NO: 20 and that comprises at least five consecutive amino acid residues counting from the C-terminal amino acid residue of that sequence. The APP signal peptide-related sequence, in addition to the amino acid sequences respectively described in SEQ ID NO: 19 and SEQ ID NO: 20, may also be a modified amino acid sequence that has the same functionality as these APP signal peptides and that is provided by a partial modification (for example, an amino acid sequence formed by the substitution in, deletion from, and/or addition (insertion) into the amino acid sequence represented by each of the preceding sequence identification numbers of one amino acid residue or a plurality (typically two or three) of amino acid residues).

In a preferred aspect of the cell growth promoter disclosed herein, the artificially synthesized peptide has, as the amino acid sequence specified by (A) (i.e., the amino acid sequence constituting a cell-penetrating peptide), an amino acid sequence represented by any of SEQ ID NOs: 1 to 18. This sequence constituting a cell-penetrating peptide, in addition to amino acid sequences as respectively described for SEQ ID NOs: 1 to 18, may also be a modified amino acid sequence that has the same functionality as these cell-penetrating peptides and that is provided by a partial modification (for example, an amino acid sequence formed by the substitution in, deletion from, and/or addition (insertion) into the amino acid sequence represented by each of the sequence identification numbers of one amino acid residue or a plurality (typically two or three) of amino acid residues).

The amino acid sequences disclosed herein for SEQ ID NOs: 1 to 18 are typical examples of the (A) an amino acid sequence constituting a cell-penetrating peptide, and can be favorably used for the execution of the present invention. It is especially preferable to employ one of the amino acid sequences (typically, SEC ID NOs: 1 to 15; especially, SEQ ID NOs: 14 and 15) that are signal sequences to localize a protein in the nucleolus within a nucleus and are known as nucleolar localization signals (NoLSs, see Non-Patent Literature 1 and 2).

In another preferred aspect of the cell growth promoter disclosed herein, the total number of amino acid residues constituting the artificially synthesized peptide is not more than 40 (for example, not more than 30). A peptide having such a short peptide chain can be easily chemically synthesized and is preferred as a component of the cell growth promoter because of its inexpensive and excellent handling characteristics.

In another preferred aspect of the cell growth promoter disclosed herein, the artificially synthesized peptide has the amino acid sequence specified by (B) at the N-terminal side of the amino acid sequence specified by (A). A peptide with such a structure has a particularly good cell growth-promoting capacity. The total number of amino acid residues constituting this peptide is particularly preferably not more than 40 (for example, not more than 30) due to the simple structure and ease of chemical synthesis.

Peptides (referred to below simply as "synthetic peptide" or "cell growth-promoting peptide") including any of the amino acid sequences in SEQ ID NOs: 21 to 62 (particularly those with not more than 40 or not more than 30 total amino acid residues), for example, peptides composed of any of the amino acid sequences in SEQ ID NOs: 21 to 62, are preferred specific examples of the artificially synthesized peptides provided by the present invention.

A cell growth promoter comprising such a synthetic peptide (cell growth-promoting peptide) is preferable for the purpose of promoting growth of cells derived from a human or other non-human mammalian origin (for instance, stem cells of one species).

The present invention, as another aspect, provides a method of producing cells or a biosynthetic substance derived from the grown cells by growing at least one type of eukaryotic cell (typically by in vivo or in vitro growth), wherein any of the cell growth promoters disclosed herein (i.e., any of the cell growth-promoting peptides disclosed herein) is supplied at least once to the eukaryotic cell subjected to proliferation.

According to such a production method, it is possible to reduce the use of an expensive cell growth factor such as bFGF or others; and therefore, a cost reduction can be achieved in cell culturing or biologically active substance production that involves cell proliferation; or the cost increase can be suppressed.

The production method disclosed herein can be preferably carried out in order to facilitate repairing or regeneration of an affected area of a subject (patient). That is, because the method disclosed herein enables efficient in-vitro proliferation of the cells that contribute to repairing or regeneration, the cells efficiently proliferated in vitro by carrying out the present method can be placed internally to the body of a subject (patient), thereby bringing about a reduction in the time for repair or regeneration.

In a preferred aspect of the production method disclosed herein, the eukaryotic cell is a cell of a human origin or a non-human mammalian origin. The cell growth-promoting peptide disclosed herein can be very favorably used to promote the growth of this type of cell. A particularly preferred example of the eukaryotic cell includes any type of undifferentiated stem cell.

DESCRIPTION OF EMBODIMENTS

Preferred embodiments of the present invention are described below. Note that technical matters other than those matters particularly mentioned in the present specification (e.g., the primary structure and chain length of a cell growth-promoting peptide) which are required for carrying out the present invention (e.g., general matters relating to peptide synthesis, cell cultivation, and preparation of a pharmaceutical composition containing a peptide) are matters of design variation that could be apprehended by a person skilled in the art based on prior art in such fields as cell engineering, medicine, pharmacology, organic chemistry, biochemistry, genetic engineering, protein engineering, molecular biology and hygieiology. The present invention can be practiced based on the technical details disclosed in the present specification and on common general technical knowledge in the pertinent fields. In the following description, amino acids are indicated by single-letter designations (in sequence listings, by three-letter designations) in accordance with the nomenclature for amino acids set forth in the IUPAC-IUB guidelines.

The entire contents of all the literature cited in this specification are incorporated by reference in this specification.

In this specification, the "artificially synthesized peptide" and "cell growth-promoting peptide" refer to a peptide fragment of which peptide chain does not by itself independently exist in a stable state in nature, that is produced by artificial chemical synthesis or biosynthesis (i.e., the production is based on genetic engineering), and that can exist in a stable state in a prescribed system (for example, a composition constituting a neuron growth promoter).

In this specification, "peptide" is a term that indicates an amino acid polymer having a plurality of peptide bonds, and, while not being limited with regard to the number of amino acid residues present in the peptide chain, it typically has a relatively small molecular weight, e.g., a total number of amino acid residues generally of not more 100 and preferably of not more than 50 (preferably not more than 40, for example, not more than 30).

In this specification, "amino acid residue", unless specifically indicated otherwise, is a term that encompasses the N-terminal amino acid and the C-terminal amino acid of the peptide chain.

In this specification, a "modified amino acid sequence" refers to an amino acid sequence formed by the substitution in, deletion from, and/or addition (insertion) into a prescribed amino acid sequence of one amino acid residue or a plurality (for example, two or three) of amino acid residues, without impairing the functionality possessed by the prescribed amino acid sequence (for example, a neuron growth-promoting capacity for the synthetic peptide). For example, a sequence produced by the conservative amino acid replacement of one or a plurality (typically two or three) of amino acid residues (for example, a sequence in which a basic amino acid residue has been replaced by a different basic amino acid residue) and a sequence produced by the addition (insertion) into or deletion from a prescribed amino acid sequence of one or a plurality (typically two or three) of amino acid residues are typical examples encompassed by the modified amino acid sequences referenced in this specification.

In this specification, "polynucleotide" is a term that indicates a polymer (a nucleic acid) in which a plurality of nucleotides are connected by the phosphodiester bond and is not limited with regard to the number of nucleotides. DNA fragments and RNA fragments of different lengths are encompassed by polynucleotides in this specification. An "artificially designed polynucleotide" refers to a polynucleotide of which nucleotide chain (full length) does not exist in nature by itself and that is artificially synthesized by chemical synthesis or biosynthesis (i.e., production based on genetic engineering).

The cell growth promoter disclosed herein is a composition that characteristically contains, as an active ingredient, the synthetic peptide discovered by the present inventors that has an excellent cell growth-promoting activity for at least one type of cell (i.e., the cell growth-promoting peptide).

As indicated above, the cell growth-promoting peptide disclosed herein has, as a partial amino acid sequence therein, an amino acid sequence constituting the cell-penetrating peptide specified as (A) above (in some cases abbreviated as the "(A) part sequence" in the following).

Any amino acid sequence constituting a cell-penetrating peptide that can traverse the cell membrane and/or nuclear membrane can be used for the (A) part sequence without particular limitation. For example, the amino acid sequences represented by SEQ ID NOs: 1 to 18 in the Sequence Listing of this Description, and their modified amino acid sequences (but limited to those that retain a cell-penetrating capability), are preferred for the amino acid sequence constituting the (A) part sequence. These are specifically as follows.

The amino acid sequence in SEQ ID NO: 1 corresponds to an NoLS composed of a total of 14 amino acid residues originating from FGF2 (basic fibroblast growth factor).

The amino acid sequence in SEQ ID NO: 2 corresponds to an NoLS composed of a total of 19 amino acid residues originating from a type of nucleolar protein (ApLLP).

The amino acid sequence in SEQ ID NO: 3 corresponds to an NoLS composed of a total of 16 amino acid residues deriving from a protein (γ(1)34.5) from herpes simplex virus type 1 (HSV-1).

The amino acid sequence in SEQ ID NO: 4 corresponds to an NoLS composed of a total of 19 amino acid residues deriving from the p40 protein of human I-mfa domain-containing protein (HIC).

The amino acid sequence in SEQ ID NO: 5 corresponds to an NoLS composed of a total of 16 amino acid residues deriving from the MEQ protein of Marek's disease virus (MDV).

The amino acid sequence in SEQ ID NO: 6 corresponds to an NoLS composed of a total of 17 amino acid residues deriving from survivin-DeltaEx3, which is a protein that inhibits apoptosis.

The amino acid sequence in SEQ ID NO: 7 corresponds to an NoLS composed of a total of 7 amino acid residues deriving from angiogenin, which is a vascular growth factor.

The amino acid sequence in SEQ ID NO: 8 corresponds to an NoLS composed of a total of 8 amino acid residues deriving from MDM2, which is a nuclear phosphoprotein that forms a complex with the p53 tumor suppressor protein.

The amino acid sequence in SEQ ID NO: 9 corresponds to an NoLS composed of a total of 9 amino acid residues deriving from GGNNVα, which is a protein from the betanoda virus.

The amino acid sequence in SEQ ID NO: 10 corresponds to an NoLS composed of a total of 7 amino acid residues deriving from NF-κB-inducing kinase (NIK).

The amino acid sequence in SEQ ID NO: 11 corresponds to an NoLS composed of a total of 15 amino acid residues deriving from nuclear VCP-like protein.

The amino acid sequence in SEQ ID NO: 12 corresponds to an NoLS composed of a total of 18 amino acid residues deriving from the nucleolar protein p120.

The amino acid sequence in SEQ ID NO: 13 corresponds to an NoLS composed of a total of 14 amino acid residues deriving from the ORF57 protein from the herpes virus saimiri (HVS).

The amino acid sequence in SEQ ID NO: 14 corresponds to an NoLS composed of a total of 13 amino acid residues, from the amino acid residue at position 491 to the amino acid residue at position 503, of the LIM kinase 2 present in human endothelial cells; this is a type of protein kinase that participates in intracellular signal transduction.

The amino acid sequence in SEQ ID NO: 15 corresponds to a nucleolar localization signal (nucleolar localization sequence) composed of a total of 8 amino acid residues present in the N protein (nucleocapsid protein) of the avian infectious bronchitis virus (IBV).

The amino acid sequence in SEQ ID NO: 16 corresponds to a cell-penetrating motif composed of a sequence with a total of 11 amino acids deriving from the protein transduction domain present in the TAT of human immunodeficiency virus (HIV).

The amino acid sequence in SEQ ID NO: 17 corresponds to a cell-penetrating motif composed of a sequence with a total of 11 amino acids of a protein transduction domain (PTD4) provided by modifying the TAT.

The amino acid sequence in SEQ ID NO: 18 corresponds to a cell-penetrating motif composed of a sequence with a total of 18 amino acids deriving from the ANT of Antennapedia, which is a mutant in *Drosophila*.

Among the preceding, NoLS-associated amino acid sequences (or their modified amino acid sequences) are particularly preferred. In particular, the NoLS-associated amino acid sequences as represented by SEQ ID NOs: 14 and 15 are particularly preferred as the (A) part sequence of the cell growth-promoting peptide.

The cell growth-promoting peptide also has the APP signal peptide-related sequence specified for the (B) (hereinafter, it may be referred to as the "(B) part sequence").

The present inventors discovered that a substantial cell growth-promoting activity can be exhibited by a relatively short peptide synthesized so as to contain an amino acid sequence that corresponds to the signal peptide of the amyloid precursor protein (APP) that is produced in the cerebral neurons of mammals, e.g., human, chimpanzee, crab-eating macaque, mouse, rat, and so forth. Investigations are currently underway on the function and operation of signal peptides (for example, refer to Non-Patent Literature 3 for a review); however, there has been no report that suggests that the growth of at least type of cell (for example, somatic stem cells such as mesenchymal stem cells and neural stem cells, embryonic stem cells, and induced pluripotent stem cells (iPS cells)) can be promoted by the use of the signal peptide sequence of the APP.

The amino acid sequences of the amyloid precursor protein signal peptide that are preferably used for the execution of the present invention are represented by the following SEQ ID NO: 19 and SEQ ID NO: 20.

The amino acid sequence given below as SEQ ID NO: 19

(SEQ ID NO: 19)
M L P G L A L L L L A A W T A R A is the signal peptide sequence composed of 17 amino acid residues from the amyloid precursor protein that is produced by cerebral neurons in the human, chimpanzee, and crab-eating macaque.

The amino acid sequence given below as SEQ ID NO: 20

(SEQ ID NO: 20)
M L P S L A L L L L A A W T V R A is the signal peptide sequence composed of 17 amino acid residues from the amyloid precursor protein that is produced by cerebral neurons in the mouse and rat.

The amino acid sequence (composed of 17 amino acid residues) represented by SEQ ID NO: 19 or in SEQ ID NO: 20 can be used as such as the (B) part sequence (the APP signal peptide-related sequence) for construction of the cell growth-promoting peptide of the present invention.

Or, an N-terminal partial amino acid sequence composed of at least five consecutive amino acid residues counting from the N-terminal amino acid residue of SEQ ID NO: 19 or SEQ ID NO: 20 can be used for the (B) part sequence, i.e., an N-terminal partial amino acid sequence that, counting from the N-terminal amino acid residue, must have from the methionine residue at position 1 to the leucine residue at position 5 (preferably to the alanine residue at position 6 and more preferably to the leucine residue at position 7) and that may use the amino acid residues on the C-terminal side beyond this, can be used as the APP signal peptide-related sequence. Thus, specific examples of the N-terminal partial amino acid sequence are as follows.

<1> N-terminal partial amino acid sequences deriving from the signal peptide sequence with SEQ ID NO: 19:

(1). counting from the N-terminal amino acid residue, the sequence composed of a total of 5 amino acid residues from the position 1 methionine residue to the position 5 leucine residue;

(2). counting from the N-terminal amino acid residue, the sequence composed of a total of 6 amino acid residues from the position 1 methionine residue to the position 6 alanine residue;

(3). counting from the N-terminal amino acid residue, the sequence composed of a total of 7 amino acid residues from the position 1 methionine residue to the position 7 leucine residue;

(4). counting from the N-terminal amino acid residue, the sequence composed of a total of 8 amino acid residues from the position 1 methionine residue to the position 8 leucine residue;

(5). counting from the N-terminal amino acid residue, the sequence composed of a total of 9 amino acid residues from the position 1 methionine residue to the position 9 leucine residue;

(6). counting from the N-terminal amino acid residue, the sequence composed of a total of 10 amino acid residues from the position 1 methionine residue to the position 10 leucine residue;

(7). counting from the N-terminal amino acid residue, the sequence composed of a total of 11 amino acid residues from the position 1 methionine residue to the position 11 alanine residue;

(8). counting from the N-terminal amino acid residue, the sequence composed of a total of 12 amino acid residues from the position 1 methionine residue to the position 12 alanine residue;

(9), counting from the N-terminal amino acid residue, the sequence composed of a total of 13 amino acid residues from the position 1 methionine residue to the position 13 tryptophan residue;

(10). counting from the N-terminal amino acid residue, the sequence composed of a total of 14 amino acid residues from the position 1 methionine residue to the position 14 threonine residue;

(11). counting from the N-terminal amino acid residue, the sequence composed of a total of 15 amino acid residues from the position 1 methionine residue to the position 15 alanine residue; and (12). counting from the N-terminal amino acid residue, the sequence composed of a total of 16 amino acid residues from the position 1 methionine residue to the position 16 arginine residue.

Among the preceding, the use is preferred in particular of a sequence composed of a total of 7 to 12 amino acid residues from, counting from the N-terminal amino acid residue, position 1 (methionine residue) to any position from position 7 (leucine residue) to position 12 (alanine residue).

<2> N-terminal partial amino acid sequences deriving from the signal peptide sequence with SEQ ID NO: 20:

(1). counting from the N-terminal amino acid residue, the sequence composed of a total of 5 amino acid residues from the position 1 methionine residue to the position 5 leucine residue;

(2). counting from the N-terminal amino acid residue, the sequence composed of a total of 6 amino acid residues from the position 1 methionine residue to the position 6 alanine residue;

(3). counting from the N-terminal amino acid residue, the sequence composed of a total of 7 amino acid residues from the position 1 methionine residue to the position 7 leucine residue;

(4). counting from the N-terminal amino acid residue, the sequence composed of a total of 8 amino acid residues from the position 1 methionine residue to the position 8 leucine residue;

(5). counting from the N-terminal amino acid residue, the sequence composed of a total of 9 amino acid residues from the position 1 methionine residue to the position 9 leucine residue;

(6). counting from the N-terminal amino acid residue, the sequence composed of a total of 10 amino acid residues from the position 1 methionine residue to the position 10 leucine residue;

(7). counting from the N-terminal amino acid residue, the sequence composed of a total of 11 amino acid residues from the position 1 methionine residue to the position 11 alanine residue;

(8). counting from the N-terminal amino acid residue, the sequence composed of a total of 12 amino acid residues from the position 1 methionine residue to the position 12 alanine residue;

(9). counting from the N-terminal amino acid residue, the sequence composed of a total of 13 amino acid residues from the position 1 methionine residue to the position 13 tryptophan residue;

(10). counting from the N-terminal amino acid residue, the sequence composed of a total of 14 amino acid residues from the position 1 methionine residue to the position 14 threonine residue;

(11). counting from the N-terminal amino acid residue, the sequence composed of a total of 15 amino acid residues from the position 1 methionine residue to the position 15 valine residue; and (12). counting from the N-terminal amino acid residue, the sequence composed of a total of 16 amino acid residues from the position 1 methionine residue to the position 16 arginine residue.

Among the preceding, the use is preferred in particular of a sequence composed of a total of 7 to 12 amino acid residues from, counting from the N-terminal amino acid residue, position 1 (methionine residue) to any position from position 7 (leucine residue) to position 12 (alanine residue).

Alternatively, a C-terminal partial amino acid sequence composed of at least five consecutive amino acid residues counting from the C-terminal amino acid residue, i.e., a C-terminal partial amino acid sequence of the signal peptide sequence in SEQ ID 19 or SEQ ID 20 that, counting from the N-terminal amino acid residue, must have from the tryptophan residue at position 13 to the alanine residue at position 17 (i.e., the C-terminal) and that may use the amino acid residues on the N-terminal side beyond this, can be used as the APP signal peptide-related sequence. Thus, specific examples of the C-terminal partial amino acid sequence are as follows.

<3> C-terminal partial amino acid sequences deriving from the signal peptide sequence with SEQ ID NO: 19:

(1). counting from the N-terminal amino acid residue, the sequence composed of a total of 5 amino acid residues from the position 13 tryptophan residue to the position 17 (C-terminal) alanine residue;

(2). counting from the N-terminal amino acid residue, the sequence composed of a total of 6 amino acid residues from the position 12 alanine residue to the position 17 (C-terminal) alanine residue;

(3). counting from the N-terminal amino acid residue, the sequence composed of a total of 7 amino acid residues from the position 11 alanine residue to the position 17 (C-terminal) alanine residue;

(4). counting from the N-terminal amino acid residue, the sequence composed of a total of 8 amino acid residues from the position 10 leucine residue to the position 17 (C-terminal) alanine residue;

(5). counting from the N-terminal amino acid residue, the sequence composed of a total of 9 amino acid residues from the position 9 leucine residue to the position 17 (C-terminal) alanine residue;

(6). counting from the N-terminal amino acid residue, the sequence composed of a total of 10 amino acid residues from the position 8 leucine residue to the position 17 (C-terminal) alanine residue;

(7). counting from the N-terminal amino acid residue, the sequence composed of a total of 11 amino acid residues from the position 7 leucine residue to the position 17 (C-terminal) alanine residue;

(8). counting from the N-terminal amino acid residue, the sequence composed of a total of 12 amino acid residues from the position 6 alanine residue to the position 17 (C-terminal) alanine residue;

(9). counting from the N-terminal amino acid residue, the sequence composed of a total of 13 amino acid residues from the position 5 leucine residue to the position 17 (C-terminal) alanine residue;

(10). counting from the N-terminal amino acid residue, the sequence composed of a total of 14 amino acid residues from the position 4 glycine residue to the position 17 (C-terminal) alanine residue;

(11). counting from the N-terminal amino acid residue, the sequence composed of a total of 15 amino acid residues from the position 3 proline residue to the position 17 (C-terminal) alanine residue; and (12). counting from the N-terminal amino acid residue, the sequence composed of a total of 16 amino acid residues from the position 2 leucine residue to the position 17 (C-terminal) alanine residue.

Among the preceding, the use is preferred in particular of a sequence composed of a total of 5 to 12 amino acid residues from, counting from the N-terminal amino acid residue, any position, from position 6 (alanine residue) to position 13 (tryptophan residue), to position 17 (alanine residue).

<4> C-terminal partial amino acid sequences deriving from the signal peptide sequence with SEQ ID NO: 20:

(1). counting from the N-terminal amino acid residue, the sequence composed of a total of 5 amino acid residues from the position 13 tryptophan residue to the position 17 (C-terminal) alanine residue;

(2). counting from the N-terminal amino acid residue, the sequence composed of a total of 6 amino acid residues from the position 12 alanine residue to the position 17 (C-terminal) alanine residue;

(3). counting from the N-terminal amino acid residue, the sequence composed of a total of 7 amino acid residues from the position 11 alanine residue to the position 17 (C-terminal) alanine residue;

(4). counting from the N-terminal amino acid residue, the sequence composed of a total of 8 amino acid residues from the position 10 leucine residue to the position 17 (C-terminal) alanine residue;

(5). counting from the N-terminal amino acid residue, the sequence composed of a total of 9 amino acid residues from the position 9 leucine residue to the position 17 (C-terminal) alanine residue;

(6). counting from the N-terminal amino acid residue, the sequence composed of a total of 10 amino acid residues from the position 8 leucine residue to the position 17 (C-terminal) alanine residue;

(7). counting from the N-terminal amino acid residue, the sequence composed of a total of 11 amino acid residues from the position 7 leucine residue to the position 17 (C-terminal) alanine residue;

(8). counting from the N-terminal amino acid residue, the sequence composed of a total of 12 amino acid residues from the position 6 alanine residue to the position 17 (C-terminal) alanine residue;

(9). counting from the N-terminal amino acid residue, the sequence composed of a total of 13 amino acid residues from the position 5 leucine residue to the position 17 (C-terminal) alanine residue;

(10). counting from the N-terminal amino acid residue, the sequence composed of a total of 14 amino acid residues from the position 4 serine residue to the position 17 (C-terminal) alanine residue;

(11). counting from the N-terminal amino acid residue, the sequence composed of a total of 15 amino acid residues from the position 3 proline residue to the position 17 (C-terminal) alanine residue; and (12). counting from the N-terminal amino acid residue, the sequence composed of a total of 16 amino acid residues from the position 2 leucine residue to the position 17 (C-terminal) alanine residue.

Among the preceding, the use is preferred in particular of a sequence composed of a total of 5 to 12 amino acid residues from, counting from the N-terminal amino acid residue, any position, from position 6 (alanine residue) to position 13 (tryptophan residue), to position 17 (alanine residue).

The peptide chain (amino acid sequence) of the cell growth-promoting peptide disclosed herein is constructed by suitably combining the previously described (A) part sequence with the previously described (B) part sequence. Either the (A) part sequence or the (B) part sequence may be positioned in relative terms at the C-terminal side (N-terminal side), but the (B) part sequence is preferably positioned at the N-terminal side of the (A) part sequence. In addition, the (A) part sequence and the (B) part sequence are preferably positioned adjoining each other. Thus, an amino acid residue not included in the two sequence portions is preferably not present between the (A) part sequence and the (B) part sequence, or, if present, preferably approximately 1 to 3 amino acid residues are present.

The cell growth-promoting peptide preferably has at least one amino acid residue that has been amidated. The structural stability of the synthetic peptide (for example, the resistance to proteases) can be improved by the amidation of the carboxyl group in an amino acid residue (typically the C-terminal amino acid residue in the peptide chain).

In particular, the following amino acid sequence is preferably used for the (A) part sequence.

```
                                           (SEQ ID NO: 14)
            K K R T L R K N D R K K R
```

The inventors discovered that—when a peptide is synthesized that contains both the amino acid sequence with SEQ ID NO: 14, which is known as a nucleolar localization signal (NoLS) as described in Non-Patent Literature 2, and an amino acid sequence constituting another, desired amino acid sequence (a relatively short sequence associated with some functionality, e.g., a peptide motif) and is added to a eukaryotic cell during cultivation—this peptide can very efficiently traverse the cell membrane of the subject cell and can also very efficiently traverse the nuclear membrane. Thus, when an artificial peptide is constructed (synthesized) by combining a desired APP signal peptide-related sequence and the amino acid sequence shown in SEQ ID NO: 14 (nucleolar localization signal-related sequence) and is added to the subject eukaryotic cell, this artificial peptide very efficiently transfers from outside the eukaryotic cell (outside the cell membrane) into the nucleus (preferably the nucleolus).

A sequence (amino acid residue) portion other than the amino acid sequences constituting the (A) part sequence and the (B) part sequence can be incorporated insofar as the cell growth-promoting activity is not impaired. While not being particularly limited, such a partial sequence is preferably a sequence that can maintain the three-dimensional shape (typically a straight-chain shape) of the (A) part sequence and (B) part sequence portions. The total number of amino acid residues constituting the peptide chain in this cell growth-promoting peptide is suitably not more than 100, desirably not more than 50, and preferably not more than 40. A synthetic peptide with a total number of amino acid residues of not more than 30 is particularly preferred.

The chemical synthesis of such a short-chain peptide is easily performed and can easily provide the cell growth-promoting peptide. The conformation (three-dimensional structure) of the peptide is not particularly limited as long as the cell growth-promoting ability is exhibited under the environment of use (in vitro or in vivo); however, a straight-chain or helical shape is preferred from the standpoint of avoiding immunogenicity (antigenicity). It is difficult for peptides with such a shape to form an epitope. Viewed from this perspective, the cell growth-promoting peptide used in the cell growth promoter preferably has a straight-chain configuration and a relatively low molecular weight (the number of amino acid residues is typically not more than 40 (particularly not more than 30)), The proportion of the (A) part sequence plus (B) part sequence with reference to the entire amino acid sequence (i.e., the number % for the number of amino acid residues constituting the (A) part sequence plus the (B) part sequence with reference to the total number of amino acid residues constituting the peptide chain) is not particularly limited insofar as the cell growth-promoting activity is not impaired, but this proportion is desirably generally at least 60%, preferably at least 80%, and particularly preferably at least 90%.

All of the amino acid residues in the cell growth-promoting peptide of the present invention are preferably L-amino acids; however, insofar as the cell growth-promoting activity is not impaired, some or all of the amino acid residues may be replaced by D-amino acids.

Among the cell growth-promoting peptides disclosed herein, those with a relatively short peptide chain can be easily produced based on general chemical synthesis methods. For example, a heretofore known solid-phase synthesis method or liquid-phase synthesis method may be used. A solid-phase synthesis method using t-butyloxycarbonyl (Boc) or 9-fluorenylmethoxycarbonyl (Fmoc) as the amino group protective group is preferred.

In the case of the cell growth-promoting peptide disclosed herein, a peptide chain having the desired amino acid sequence and modified (for example, C-terminal amidation) portions can be synthesized by a solid-phase synthesis method using a commercially available peptide synthesizer (available, for example, from PerSeptive Biosystems and Applied Biosystems).

Alternatively, the cell growth-promoting peptide can be biosynthesized based on genetic engineering techniques. This approach is suitable for the production of peptides having a relatively long peptide chain that are generally referred to as polypeptides. Thus, a DNA is synthesized that has a nucleotide sequence (including the ATG start codon) coding for the amino acid sequence of the desired cell growth-promoting peptide. A recombinant vector having an expression genetic construct comprising this DNA and the various regulatory elements for the expression of the amino acid sequence in a host cell (including a promoter, ribosome binding site, terminator, enhancer, and various cis elements that regulate the expression level) is constructed in conformity to the host cell.

Using general techniques, this recombinant vector is introduced into a particular host cell (for example, yeast or an insect cell) and the host cell or a tissue or individual containing this cell is grown under prescribed conditions. The desired polypeptide can be expressed and produced within the cell as a result. The subject cell growth-promoting peptide can be obtained by isolating the polypeptide from the host cell (from the medium in the case of secretion) and purification.

The methods heretofore practiced in the pertinent fields may be used as such for, for example, the method of constructing the recombinant vector and the method of introducing the constructed recombinant vector into the host cell, and, since these methods as such are not characteristic features of the present invention, their detailed description has been omitted.

For example, a fusion protein expression system can be used to bring about the efficient production of large amounts within a host cell. Thus, a gene (DNA) encoding the amino acid sequence of the desired cell growth-promoting peptide is chemically synthesized and this synthetic gene is introduced into a suitable site in a suitable fusion protein expression vector (for example, a glutathione S-transferase (GST) fusion protein expression vector such as the pET series available from Novagen and the pGEX series available from Amersham Biosciences). Host cells (typically, *Escherichia coli*) is then transformed by this vector. The desired fusion protein is produced by cultivating the resulting transformant. This protein is then extracted and purified. The resulting purified fusion protein is subsequently cleaved with a prescribed enzyme (protease) and the freed target peptide fragment (the designed cell growth-promoting peptide) is recovered by a method such as affinity chromatography. The cell growth-promoting peptide of the present invention can be produced using such a heretofore known fusion protein expression system (for example, the GST/His system available from Amersham Biosciences can be used).

Alternatively, the target polypeptide may be synthesized in vitro by constructing a template DNA for a cell-free protein synthesis system (i.e., a synthesized gene fragment having a nucleotide sequence which codes for the amino acid sequence of the cell growth-promoting peptide) and, using the various compounds required for peptide synthesis (e.g., ATP, RNA polymerase, amino acids, etc.), and employing a cell-free protein synthesis system. For information concerning cell-free protein synthesis systems, reference may be made to, for example, Shimizu et al., *Nature Biotechnology*, 19, 751-755 (2001), and Madin et al., *Proc. Natl. Acad. Sci. USA,* 97(2), 559-564 (2000). Based on the technology described in these articles, many corporations have been conducting contract manufacturing of polypeptides at the time when this application was filed. Also, wheat germ cell-free protein synthesis kits (such as PROTEIOST™ available from Toyobo Co., Ltd. of Japan) are commercially available.

Therefore, so long as the (A) part sequence and the (B) part sequence have been selected and the peptide chain has been designed, the subject cell growth-promoting peptide can be easily synthesized and produced by a cell-free protein synthesis system in accordance with the amino acid sequence. For instance, a cell growth-promoting peptide of the present invention can be easily produced based on PURESYSTEM (registered trademark) from Post Genome Institute Co., Ltd, of Japan.

A single-stranded or double-stranded polynucleotide containing the nucleotide sequence encoding the cell growth-promoting peptide disclosed herein and/or the nucleotide sequence complementary to that nucleotide sequence, can be easily produced (synthesized) by heretofore known methods. Thus, a nucleotide sequence that corresponds to the amino acid sequence of the cell growth-promoting peptide can easily be determined and provided by selecting the codons that correspond to the individual amino acid resides that constitute the designed amino acid sequence. Once the nucleotide sequence has been determined, a polynucleotide (single strand) corresponding to the desired nucleotide sequence can be readily obtained using, for example, a DNA synthesizer. Then, using the resulting single-stranded DNA as a template, the desired double-stranded DNA can be obtained using various enzymatic synthesis techniques (typically PCR).

The polynucleotide provided by the present invention may be in the form of DNA or RNA (mRNA or the like). The DNA can be provided in the form of a double strand or a single strand. When it is provided in the form of a single strand, it may be a coding strand (sense strand) or may be an anticoding strand (anti-sense strand) that is complementary thereto.

The polynucleotide provided in accordance with the present invention can be used as a starting material for the construction of a recombinant gene (expression cassette) for the production, as described above, of the cell growth-promoting peptide in various hosts or using a cell-free protein synthesis system.

In accordance with the present invention, a polynucleotide is provided that contains a nucleotide sequence coding for a cell growth-promoting peptide with a novel amino acid sequence, and/or that contains a nucleotide sequence complementary to that nucleotide sequence. For example, an artificially designed polynucleotide is provided that contains (or is substantially constituted of) a nucleotide sequence coding for an amino acid sequence represented by SEQ ID NOs: 21 to 62 in which the total number of amino acid residues constituting the peptide chain is not more than 50 (preferably not more than 40, for example, not more than 30), or coding for an amino acid sequence provided by modifying such an amino acid sequence, or coding for an amino acid sequence that contains such an amino acid sequence, and/or that contains (or is substantially constituted of) a nucleotide sequence complementary to the nucleotide sequence.

A preferred cell growth-promoting peptide of the present invention has a high cell growth-promoting activity for at least one type of eukaryotic cell. As a consequence, it can be favorably used as an active ingredient in a cell growth promoter. Insofar as the cell growth-promoting activity is not impaired, the cell growth-promoting peptide present in the cell growth promoter may be in the form of a salt. For example, an acid-addition salt of the peptide can be used; this can be obtained by carrying out an addition reaction by the usual methods with an inorganic acid or organic acid as is ordinarily used. Or, other salts (for example, metal salts) may be used as long as a cell growth-promoting activity is present. The "peptide" described in this specification and in the Claims encompasses peptides in these salt forms.

The cell growth promoter disclosed herein can contain various pharmaceutically (medicinally) permissible carriers in conformity to the form of use, insofar as the cell growth-promoting peptide, which is an active ingredient, is maintained in a state in which its cell growth-promoting activity is not impaired. Carriers generally used as diluents or excipients in peptide medications are preferred. Although it may suitably vary depending on the intended purpose and form of the cell proliferation promoter, typical examples include water, physiological buffers and various organic solvents. The carrier may be an aqueous alcohol (ethanol or the like) solution at an appropriate concentration, glycerol, or non-drying oil such as olive oil. Or it may be a liposome. Examples of secondary ingredients that may be contained in the cell proliferation promoter include various fillers, thickeners, binders, wetting agents, surfactants, dyes, fragrances and the like.

The form of the cell proliferation promoter is not subject to any particular limitation. Examples of typical forms include liquid formulas, suspensions, emulsions, aerosols, foams, granules, powders, tablets, capsules, ointments, aqueous gels and the like. For use in injection or the like, the cell proliferation promoter may be rendered into a freeze-dried form or pellets to be prepared into a drug solution by dissolving in saline or a suitable buffer (e.g., PBS) just prior to use.

The process itself of preparing a drug (composition) in various forms by using as the materials the cell proliferation-promoting peptide (main ingredient) and various carriers (secondary ingredients) may be carried out in accordance with a conventional method. Because such a preparation process itself is not distinctive to the present invention, a detailed description is omitted here. An example of a detailed information source relating to formulation is *Comprehensive Medicinal Chemistry*, edited by Corwin Hansch and published by Pergamon Press (1990), the entire contents of which are incorporated in this specification by reference.

The subject cells to which the cell proliferation promoter (cell proliferation-promoting peptide) disclosed herein is applied are not particularly limited, with the promoter being able to enhance the proliferation ability of eukaryotic cells of various living species In particular, cells from human and from non-human animals (particularly mammals) are a preferred subject for application. Stem cells are a particularly preferred subject from the standpoint of the medical value. These stem cells can be exemplified by embryonic stem cells, induced pluripotent stem cells (iPS cells), mesenchymal stem cells, neural stem cells, bone marrow stem cells, and hematopoietic stem cells. Other examples preferred as the subject include somatic cells (dermal fibroblasts, neural cells, vascular endothelial cells and the like) and germ cells. From the standpoint of cell proliferation, using stem cells in an undifferentiated state (stem cells that had not been subjected to differentiation-inducing treatment) is particularly preferable.

The cell growth promoter disclosed herein can be used at a dose and by a method that correspond to its form and purpose.

For example, when growth is carried out by in vitro cultivation of the cells (for example, an established cell line), a suitable amount of the cell growth-promoting peptide disclosed herein (i.e., the cell growth promoter containing this peptide) may be added to the culture medium for the eukaryotic cells that are the cultivation (growth) subject at any stage in the cultivation sequence and preferably at the same time as the start of cultivation and/or in a stage soon after the start of cultivation.

The amount of addition and the number of times of addition are not particularly limited since they will vary as a function of conditions such as the type of cell being cultivated, the cell density (the cell density at the start of cultivation), the passage number, the cultivation conditions, the type of culture medium, and so forth. However, for the cultivation of a typical eukaryotic cell (particularly a cell from a mammal, including human), preferably from one addition to a plurality of additions (for example, at the start of cultivation with supplementary additions accompanying cell passage and medium exchange) is made in order to bring the concentration of the cell growth-promoting peptide in the medium generally into the range from 0.1 μM to 100 μM and preferably into the range from 0.5 μM to 20 μM (for example, 1 μM to 10 μM).

By adding the cell growth promoter (cell growth-promoting peptide) disclosed herein to an in-vitro culturing medium, the subject cells themselves or the biosynthetic substances (e.g., various physiologically active agents and enzymes) produced by the said cells can be efficiently manufactured. Moreover, since an expensive growth factor such as bFGF or the like is not used or a smaller amount thereof may be used, the manufacturing cost can be reduced.

In another case where cells (e.g., a tissue fragment or a cellular mass transplanted in a specific area) are proliferated in vivo, an appropriate amount of the cell proliferation promoter (i.e., cell proliferation-promoting peptide) disclosed herein can be prepared into a liquid formula and administered by a desired amount to a patient (i.e. in vivo) by intravenous, intramuscular, subcutaneous, intradermal, or intraperitoneal injection. Alternatively, the promoter in a solid form such as tablets, a gel form such as ointment and the like, or an aqueous gel form can be administered directly to an affected area (e.g., body surface such as a burn or a wound). Alternatively, it can be administered orally or in a suppository form. In these ways, the proliferation rate of the subject cells to be grown in vivo, typically in an affected area or its periphery can be increased. The added amount and the number of added portions are not particularly limited as they may vary depending on the conditions such as the type of the cells to be proliferated, present area, and the like.

By administering the cell proliferation promoter (cell proliferation-promoting peptide) disclosed herein to a needy area in vivo, its cell proliferation-promoting activity can enhance nerve regeneration, angiogenesis, skin regeneration or the like. By the increased cell proliferation capability, for instance, anti-aging of skin, early fixation of a transplanted organ, early reparation of a wound or a burn caused by a physical interference such as an traffic accident or the like can be accomplished. Additionally, for example, the promoter can be used as a pharmaceutical composition that contributes to regenerative medicine treatment of neural diseases such as Parkinson's disease, stroke, Alzheimer's disease, body paralysis caused by spinal cord injury, cerebral contusion, amyotrophic lateral sclerosis, Huntington's disease, brain tumor, retinal degeneration and the like.

Alternatively, by adding an appropriate amount of a cell proliferation promoter (cell proliferation-promoting peptide) to a cellular material removed temporarily or permanently from an organism, i.e., a living tissue or a cellular mass (e.g., a material cultured from somatic stem cells), the subject cells (even some tissue or an organ) can be efficiently produced in vitro without using a large amount of an expensive growth factor such as bFGF or the like.

By placing the subject cells (or some tissue or an organ in which the number of cells had been increased) that had been efficiently produced (proliferated) in vitro by employing the cell production method (in-vitro cell production method) or the cell proliferation promoter disclosed herein to a lesion (i.e., inside a patient's body) where repair or regeneration is needed, the time required for the repair or the regeneration can be reduced.

EXAMPLE 1

Peptide Synthesis

A total of 21 peptides (samples 1 to 21) were prepared using the subsequently described peptide synthesizer. Data on these synthesized peptides, e.g., the amino acid sequence and so forth, is represented by Tables 1 and 2.

TABLE 1

| sample no. | amino acid sequence | total number of amino acid residues |
| --- | --- | --- |
| 1 | MLPSLALLLLAAWTVRAGKKRTLRKNDRKKR (SEQ ID NO: 21) | 31 |

TABLE 1-continued

| sample no. | amino acid sequence | total number of amino acid residues |
| --- | --- | --- |
| 2 | PSLALLLLAAWTVRAGKKRTLRKNDRKKR (SEQ ID NO: 22) | 29 |
| 3 | SLALLLLAAWTVRAGKKRTLRKNDRKKR (SEQ ID NO: 23) | 28 |
| 4 | LALLLLAAWTVRAGKKRTLRKNDRKKR (SEQ ID NO: 24) | 27 |
| 5 | ALLLLAAWTVRAGKKRTLRKNDRKKR (SEQ ID NO: 25) | 26 |
| 6 | LLLLAAWTVRAGKKRTLRKNDRKKR (SEQ ID NO: 26) | 25 |
| 7 | LLLAAWTVRAGKKRTLRKNDRKKR (SEQ ID NO: 27) | 24 |
| 8 | LLAAWTVRAGKKRTLRKNDRKKR (SEQ ID NO: 28) | 23 |
| 9 | LAAWTVRAGKKRTLRKNDRKKR (SEQ ID NO: 29) | 22 |
| 10 | AAWTVRAGKKRTLRKNDRKKR (SEQ ID NO: 30) | 21 |
| 11 | AWTVRAGKKRTLRKNDRKKR (SEQ ID NO: 31) | 20 |
| 12 | WTVRAGKKRTLRKNDRKKR (SEQ ID NO: 32) | 19 |

TABLE 2

| sample no. | amino acid sequence | total number of amino acid residues |
| --- | --- | --- |
| 13 | MLPSLALLLLAAWTVGKKRTLRKNDRKKR (SEQ ID NO: 33) | 29 |
| 14 | MLPSLALLLLAAWTGKKRTLRKNDRKKR (SEQ ID NO: 34) | 28 |
| 15 | MLPSLALLLLAAWGKKRTLRKNDRKKR (SEQ ID NO: 35) | 27 |
| 16 | MLPSLALLLLAAGKKRTLRKNDRKKR (SEQ ID NO: 36) | 26 |
| 17 | MLPSLALLLLAGKKRTLRKNDRKKR (SEQ ID NO: 37) | 25 |

TABLE 2-continued

| sample no. | amino acid sequence | total number of amino acid residues |
|---|---|---|
| 18 | MLPSLALLLLGKKRTLRKNDRKKR (SEQ ID NO: 38) | 24 |
| 19 | MLPSLALLLGKKRTLRKNDRKKR (SEQ ID NO: 39) | 23 |
| 20 | MLPSLALLGKKRTLRKNDRKKR (SEQ ID NO: 40) | 22 |
| 21 | MLPSLALGKKRTLRKNDRKKR (SEQ ID NO: 41) | 21 |

As shown in Tables 1 and 2, each sample peptide is a chemically synthesized straight-chain peptide composed in its entirety of not more than 40 amino acid residues and specifically composed of from 19 to 31 amino acid residues, and constructed so as to have the previously described amino acid sequence from LIM kinase 2 represented by SEQ ID NO: 14 (NoLS) at the C-terminal side of each particular peptide chain, an amino acid sequence deriving from the APP signal peptide represented by SEQ ID NO: 19 or SEQ ID NO: 20 at the N-terminal side, and a linker of one glycine residue interposed therebetween.

Samples 1 to 21 have, on the N-terminal side from the glycine linker, the APP signal peptide sequence represented by SEQ ID NO: 20 or a partial amino acid sequence selected from that sequence.

Thus, sample 1 has, as its APP signal peptide-related sequence, the entire amino acid sequence (a total of 17 amino acid residues) of the signal peptide with SEQ ID NO: 20.

Sample 2 has, as its APP signal peptide-related sequence, a C-terminal partial amino acid sequence composed of a total of 15 amino acid residues, from the position 3 proline residue to the position 17 (C terminal) alanine residue counting from the N-terminal amino acid residue of the signal peptide sequence with SEQ ID NO: 20.

Sample 3 has, as its APP signal peptide-related sequence, a C-terminal partial amino acid sequence composed of a total of 14 amino acid residues, from the position 4 serine residue to the position 17 (C terminal) alanine residue counting from the N-terminal amino acid residue of the signal peptide sequence with SEQ ID NO: 20.

Sample 4 has, as its APP signal peptide-related sequence, a C-terminal partial amino acid sequence composed of a total of 13 amino acid residues, from the position 5 leucine residue to the position 17 (C terminal) alanine residue counting from the N-terminal amino acid residue of the signal peptide sequence with SEQ ID NO: 20.

Sample 5 has, as its APP signal peptide-related sequence, a C-terminal partial amino acid sequence composed of a total of 12 amino acid residues, from the position 6 alanine residue to the position 17 (C terminal) alanine residue counting from the N-terminal amino acid residue of the signal peptide sequence with SEQ ID NO: 20.

Sample 6 has, as its APP signal peptide-related sequence, a C-terminal partial amino acid sequence composed of a total of 11 amino acid residues, from the position 7 leucine residue to the position 17 (C terminal) alanine residue counting from the N-terminal amino acid residue of the signal peptide sequence with SEQ ID NO: 20.

Sample 7 has, as its APP signal peptide-related sequence, a C-terminal partial amino acid sequence composed of a total of 10 amino acid residues, from the position 8 leucine residue to the position 17 (C terminal) alanine residue counting from the N-terminal amino acid residue of the signal peptide sequence with SEQ ID NO: 20.

Sample 8 has, as its APP signal peptide-related sequence, a C-terminal partial amino acid sequence composed of a total of 9 amino acid residues, from the position 9 leucine residue to the position 17 (C terminal) alanine residue counting from the N-terminal amino acid residue of the signal peptide sequence with SEQ ID NO: 20.

Sample 9 has, as its APP signal peptide-related sequence, a C-terminal partial amino acid sequence composed of a total of 8 amino acid residues, from the position 10 leucine residue to the position 17 (C terminal) alanine residue counting from the N-terminal amino acid residue of the signal peptide sequence with SEQ ID NO: 20.

Sample 10 has, as its APP signal peptide-related sequence, a C-terminal partial amino acid sequence composed of a total of 7 amino acid residues, from the position 11 alanine residue to the position 17 (C terminal) alanine residue counting from the N-terminal amino acid residue of the signal peptide sequence with SEQ ID NO: 20.

Sample 11 has, as its APP signal peptide-related sequence, a C-terminal partial amino acid sequence composed of a total of 6 amino acid residues, from the position 12 alanine residue to the position 17 (C terminal) alanine residue counting from the N-terminal amino acid residue of the signal peptide sequence with SEQ ID NO: 20.

Sample 12 has, as its APP signal peptide-related sequence, a C-terminal partial amino acid sequence composed of a total of 5 amino acid residues, from the position 13 tryptophan residue to the position 17 (C terminal) alanine residue counting from the N-terminal amino acid residue of the signal peptide sequence with SEQ ID NO: 20.

Sample 13 has, as its APP signal peptide-related sequence, an N-terminal partial amino acid sequence composed of a total of 15 amino acid residues, from the position 1 methionine residue to the position 15 valine residue counting from the N-terminal amino acid residue of the signal peptide sequence with SEQ ID NO: 20.

Sample 14 has, as its APP signal peptide-related sequence, an N-terminal partial amino acid sequence composed of a total of 14 amino acid residues, from the position 1 methionine residue to the position 14 threonine residue counting from the N-terminal amino acid residue of the signal peptide sequence with SEQ ID NO: 20.

Sample 15 has, as its APP signal peptide-related sequence, an N-terminal partial amino acid sequence composed of a total of 13 amino acid residues, from the position 1 methionine residue to the position 13 tryptophan residue counting from the N-terminal amino acid residue of the signal peptide sequence with SEQ ID NO: 20.

Sample 16 has, as its APP signal peptide-related sequence, an N-terminal partial amino acid sequence composed of a total of 12 amino acid residues, from the position 1 methionine residue to the position 12 alanine residue counting from the N-terminal amino acid residue of the signal peptide sequence with SEQ ID NO: 20.

Sample 17 has, as its APP signal peptide-related sequence, an N-terminal partial amino acid sequence composed of a total of 11 amino acid residues, from the position 1 methionine residue to the position 11 alanine residue counting from the N-terminal amino acid residue of the signal peptide sequence with SEQ ID NO: 20.

Sample 18 has, as its APP signal peptide-related sequence, an N-terminal partial amino acid sequence composed of a total of 10 amino acid residues, from the position 1 methionine residue to the position 10 leucine residue counting from the N-terminal amino acid residue of the signal peptide sequence with SEQ ID NO: 20.

Sample 19 has, as its APP signal peptide-related sequence, an N-terminal partial amino acid sequence composed of a total of 9 amino acid residues, from the position 1 methionine residue to the position 9 leucine residue counting from the N-terminal amino acid residue of the signal peptide sequence with SEQ ID NO: 20.

Sample 20 has, as its APP signal peptide-related sequence, an N-terminal partial amino acid sequence composed of a total of 8 amino acid residues, from the position 1 methionine residue to the position 8 leucine residue counting from the N-terminal amino acid residue of the signal peptide sequence with SEQ ID NO: 20.

Sample 21 has, as its APP signal peptide-related sequence, an N-terminal partial amino acid sequence composed of a total of 7 amino acid residues, from the position 1 methionine residue to the position 7 leucine residue counting from the N-terminal amino acid residue of the signal peptide sequence with SEQ ID NO: 20.

In all of these peptides, the carboxyl group (—COOH) of the C-terminal amino acid is amidated (—CONH$_2$). Each of these peptides was synthesized by solid-phase synthesis (Fmoc chemistry) using a commercial peptide synthesizer (an intavis AG system) in accordance with its operation manual. Because the mode of using a peptide synthesizer itself is not distinctive to the present invention, a detailed description is omitted here.

EXAMPLE 2

Evaluation of the Cell Growth-Promoting Activity of the Synthetic Peptides

Experimental sections were set up that used the cell growth-promoting peptides obtained in Example 1 (samples 1 to 21) as a cell growth promoter and that used a commercially available bFGF as a cell growth promoter as a comparative example. For the control, a peptide-free section (the bFGF was also not added) was set up.

The details of the evaluation testing are provided below. Each synthesized sample peptide was dissolved in PBS (phosphate-buffered physiological saline) to prepare a stock solution with a peptide concentration of 1 mM.

Rat bone marrow-derived stem cells (mesenchymal stem cells) were used as the test cells. Specifically, the test stem cells were cultured by passage on Dulbecco's MEM medium (DMEM medium: Gibco product) containing 10% fetal bovine serum (FBS: Gibco product), 2 mM of L-glutamine, 50 unit/mL of penicillin, and 50 μg/mL of streptomycin. From the second passage to the fourth passage (passages 2 to 4) were used in this evaluation testing.

Thus, the test stem cells were preliminarily recovered by treatment with a 0.05% trypsin-0.53 mM EDTA solution; a test stem cell solution, prepared with the DMEM medium containing 10 ng/mL of bFGF to provide 1×10$^4$ cells/mL, was seeded to each well of a 96-well plate to provide a cell count of 1×10$^3$ per well; and pre-cultivation was carried out overnight. The amount of medium was brought to 100 μL per well for this.

The medium in each well was then exchanged for fresh medium to which a stock solution of a peptide selected from sample 1 to 21 had been added, so as to give a concentration of the peptide in each well of approximately 2 μM. For comparison, in some wells the medium in the well was exchanged for fresh medium to which a commercially available bFGF (product of PeproTech) had been added to give a concentration of 10 ng/mL (the bFGF experimental section in Table 3). Wells were also set up that did not contain bFGF or any sample peptide (the control section in Table 3).

After the addition of the sample peptide or bFGF as indicated above, the 96-well plate was placed in a CO$_2$ incubator and cultivation at quiescence was carried out at 37° C. under 5% CO$_2$. Medium exchange was performed every other day. The exchange medium was the same as that used at the start of cultivation (i.e., the same sample peptide or bFGF was also added to the exchange medium as in the sample peptide addition section or bFGF addition section).

During this cultivation test, a "water-soluble tetrazolium salt (WST-8)" was added as a chromogenic reagent to some wells at the start of cultivation (day 0), at two days after the start of cultivation (day 2), and at four days after the start of cultivation (day 4). After incubation for 2 hours after the addition, the cell culture fluid to which the chromogenic reagent had been added was recovered. The extent of cell growth was evaluated by a colorimetric method in which, based on reduction of the tetrazolium salt, the absorbance (OD$_{450}$) at a wavelength of 450 nm was measured. The results are represented by Table 3.

TABLE 3

| | OD450 | | |
|---|---|---|---|
| sample no. | at the start of cultivation | after 2 days | after 4 days |
| 1 | 0.058 | 0.132 | 0.243 |
| 2 | 0.058 | 0.136 | 0.297 |
| 3 | 0.058 | 0.139 | 0.293 |
| 4 | 0.058 | 0.136 | 0.304 |
| 5 | 0.058 | 0.189 | 0.483 |
| 6 | 0.058 | 0.186 | 0.483 |
| 7 | 0.058 | 0.176 | 0.499 |
| 8 | 0.058 | 0.168 | 0.418 |
| 9 | 0.058 | 0.179 | 0.398 |
| 10 | 0.058 | 0.149 | 0.389 |
| 11 | 0.058 | 0.169 | 0.403 |
| 12 | 0.058 | 0.181 | 0.388 |
| 13 | 0.058 | 0.123 | 0.232 |
| 14 | 0.058 | 0.132 | 0.293 |
| 15 | 0.058 | 0.133 | 0.276 |
| 16 | 0.058 | 0.172 | 0.525 |
| 17 | 0.058 | 0.176 | 0.468 |
| 18 | 0.058 | 0.184 | 0.505 |
| 19 | 0.058 | 0.163 | 0.478 |
| 20 | 0.058 | 0.158 | 0.320 |
| 21 | 0.058 | 0.155 | 0.332 |
| bFGF | 0.058 | 0.196 | 0.484 |
| control (no addition) | 0.058 | 0.114 | 0.205 |

As is clear from the absorbance values shown in Table 3, the cultivation sections containing the cell growth-promoting peptide disclosed herein (samples 1 to 21) were seen to have an increase in cell growth performance that was the same as for the cultivation section to which bFGF was added. This shows that these sample peptides are peptides that have a very good cell growth-promoting activity.

In particular, when compared to the addition of bFGF, samples 5 to 12 and samples 16 to 21 had particularly significant cell growth-promoting activities. Normal bone differentiation was seen when the test stem cells grown/produced in these examples were recovered and subjected to a general treatment to induce bone differentiation in this type of stem cell using commercially available materials. This demonstrates that the cell growth-promoting peptide disclosed herein (cell growth promoter) can promote normal cell growth without causing abnormalities (for example, malignant transformation) in the cells subjected for growth.

While the detailed data has not been provided, the same increase in cell growth performance as in these examples was also seen when neural stem cells were used as the subject instead of mesenchymal stem cells as above.

EXAMPLE 3

Granule Preparation 50 mg of the sample 1 peptide was mixed with 50 mg crystalline cellulose and 400 mg lactose; 1 mL of a mixed solution of ethanol and water was added; and mixing/kneading was carried out. The resulting mixture was granulated by a standard method to obtain granules (i.e., a granular cell growth promoter) in which the base component was the cell growth-promoting peptide.

EXAMPLE 4

Peptide Synthesis

A total of 21 peptides (samples 22 to 42) were prepared using the subsequently described peptide synthesizer. Data on these synthesized peptides, e.g., the amino acid sequence and so forth, is represented by Tables 4 and 5.

TABLE 4

| sample no. | amino acid sequence | total number of amino acid residues |
|---|---|---|
| 22 | MLPGLALLLLAAWTARAGKKRTLRKNDRKKR (SEQ ID NO: 42) | 31 |
| 23 | PGLALLLLAAWTARAGKKRTLRKNDRKKR (SEQ ID NO: 43) | 29 |
| 24 | GLALLLLAAWTARAGKKRTLRKNDRKKR (SEQ ID NO: 44) | 28 |
| 25 | LALLLLAAWTARAGKKRTLRKNDRKKR (SEQ ID NO: 45) | 27 |
| 26 | ALLLLAAWTARAGKKRTLRKNDRKKR (SEQ ID NO: 46) | 26 |
| 27 | LLLLAAWTARAGKKRTLRKNDRKKR (SEQ ID NO: 47) | 25 |
| 28 | LLLAAWTARAGKKRTLRKNDRKKR (SEQ ID NO: 48) | 24 |
| 29 | LLAAWTARAGKKRTLRKNDRKKR (SEQ ID NO: 49) | 23 |

TABLE 4-continued

| sample no. | amino acid sequence | total number of amino acid residues |
|---|---|---|
| 30 | LAAWTARAGKKRTLRKNDRKKR (SEQ ID NO: 50) | 22 |
| 31 | AAWTARAGKKRTLRKNDRKKR (SEQ ID NO: 51) | 21 |
| 32 | AWTARAGKKRTLRKNDRKKR (SEQ ID NO: 52) | 20 |
| 33 | WTARAGKKRTLRKNDRKKR (SEQ ID NO: 53) | 19 |

TABLE 5

| sample no. | amino acid sequence | total number of amino acid residues |
|---|---|---|
| 34 | MLPGLALLLLAAWTAGKKRTLRKNDRKKR (SEQ ID NO: 54) | 29 |
| 35 | MLPGLALLLLAAWTGKKRTLRKNDRKKR (SEQ ID NO: 55) | 28 |
| 36 | MLPGLALLLLAAWGKKRTLRKNDRKKR (SEQ ID NO: 56) | 27 |
| 37 | MLPGLALLLLAAGKKRTLRKNDRKKR (SEQ ID NO: 57) | 26 |
| 38 | MLPGLALLLLAGKKRTLRKNDRKKR (SEQ ID NO: 58) | 25 |
| 39 | MLPGLALLLLGKKRTLRKNDRKKR (SEQ ID NO: 59) | 24 |
| 40 | MLPGLALLLGKKRTLRKNDRKKR (SEQ ID NO: 60) | 23 |
| 41 | MLPGLALLGKKRTLRKNDRKKR (SEQ ID NO: 61) | 22 |
| 42 | MLPGLALGKKRTLRKNDRKKR (SEQ ID NO: 62) | 21 |

As shown in Tables 4 and 5, each sample peptide is a chemically synthesized straight-chain peptide composed in its entirety of not more than 40 amino acid residues and specifically composed of from 19 to 31 amino acid residues, and constructed so as to have the previously described amino acid sequence from LIM kinase 2 represented by SEQ ID NO: 14 (NoLS) at the C-terminal side of each particular peptide chain, an amino acid sequence deriving from the APP signal peptide represented by SEQ ID NO: 19 or SEQ ID NO: 20 at the N-terminal side, and a linker of one glycine residue interposed therebetween.

Samples 22 to 42 have, on the N-terminal side from the glycine linker, the APP signal peptide sequence represented by SEQ ID NO: 19 or a partial amino acid sequence selected from that sequence.

Thus, sample 22 has, as its APP signal peptide-related sequence, the entire amino acid sequence (a total of 17 amino acid residues) of the signal peptide with SEQ ID NO: 19.

Sample 23 has, as its APP signal peptide-related sequence, a C-terminal partial amino acid sequence composed of a total of 15 amino acid residues, from the position 3 proline residue to the position 17 (C terminal) alanine residue counting from the N-terminal amino acid residue of the signal peptide sequence with SEQ ID NO: 19.

Sample 24 has, as its APP signal peptide-related sequence, a C-terminal partial amino acid sequence composed of a total of 14 amino acid residues, from the position 4 glycine residue to the position 17 (C terminal) alanine residue counting from the N-terminal amino acid residue of the signal peptide sequence with SEQ ID NO: 19.

Sample 25 has, as its APP signal peptide-related sequence, a C-terminal partial amino acid sequence composed of a total of 13 amino acid residues, from the position 5 leucine residue to the position 17 (C terminal) alanine residue counting from the N-terminal amino acid residue of the signal peptide sequence with SEQ ID NO: 19.

Sample 26 has, as its APP signal peptide-related sequence, a C-terminal partial amino acid sequence composed of a total of 12 amino acid residues, from the position 6 alanine residue to the position 17 (C terminal) alanine residue counting from the N-terminal amino acid residue of the signal peptide sequence with SEQ ID NO: 19.

Sample 27 has, as its APP signal peptide-related sequence, a C-terminal partial amino acid sequence composed of a total of 11 amino acid residues, from the position 7 leucine residue to the position 17 (C terminal) alanine residue counting from the N-terminal amino acid residue of the signal peptide sequence with SEQ ID NO: 19.

Sample 28 has, as its APP signal peptide-related sequence, a C-terminal partial amino acid sequence composed of a total of 10 amino acid residues, from the position 8 leucine residue to the position 17 (C terminal) alanine residue counting from the N-terminal amino acid residue of the signal peptide sequence with SEQ ID NO: 19.

Sample 29 has, as its APP signal peptide-related sequence, a C-terminal partial amino acid sequence composed of a total of 9 amino acid residues, from the position 9 leucine residue to the position 17 (C terminal) alanine residue counting from the N-terminal amino acid residue of the signal peptide sequence with SEQ ID NO: 19.

Sample 30 has, as its APP signal peptide-related sequence, a C-terminal partial amino acid sequence composed of a total of 8 amino acid residues, from the position 10 leucine residue to the position 17 (C terminal) alanine residue counting from the N-terminal amino acid residue of the signal peptide sequence with SEQ ID NO: 19.

Sample 31 has, as its APP signal peptide-related sequence, a C-terminal partial amino acid sequence composed of a total of 7 amino acid residues, from the position 11 alanine residue to the position 17 (C terminal) alanine residue counting from the N-terminal amino acid residue of the signal peptide sequence with SEQ ID NO: 19.

Sample 32 has, as its APP signal peptide-related sequence, a C-terminal partial amino acid sequence composed of a total of 6 amino acid residues, from the position 12 alanine residue to the position 17 (C terminal) alanine residue counting from the N-terminal amino acid residue of the signal peptide sequence with SEQ ID NO: 19.

Sample 33 has, as its APP signal peptide-related sequence, a C-terminal partial amino acid sequence composed of a total of 5 amino acid residues, from the position 13 tryptophan residue to the position 17 (C terminal) alanine residue counting from the N-terminal amino acid residue of the signal peptide sequence with SEQ ID NO: 19.

Sample 34 has, as its APP signal peptide-related sequence, an N-terminal partial amino acid sequence composed of a total of 15 amino acid residues, from the position 1 methionine residue to the position 15 alanine residue counting from the N-terminal amino acid residue of the signal peptide sequence with SEQ ID NO: 19.

Sample 35 has, as its APP signal peptide-related sequence, an N-terminal partial amino acid sequence composed of a total of 14 amino acid residues, from the position 1 methionine residue to the position 14 threonine residue counting from the N-terminal amino acid residue of the signal peptide sequence with SEQ ID NO: 19.

Sample 36 has, as its APP signal peptide-related sequence, an N-terminal partial amino acid sequence composed of a total of 13 amino acid residues, from the position 1 methionine residue to the position 13 tryptophan residue counting from the N-terminal amino acid residue of the signal peptide sequence with SEQ ID NO: 19.

Sample 37 has, as its APP signal peptide-related sequence, an N-terminal partial amino acid sequence composed of a total of 12 amino acid residues, from the position 1 methionine residue to the position 12 alanine residue counting from the N-terminal amino acid residue of the signal peptide sequence with SEQ ID NO: 19.

Sample 38 has, as its APP signal peptide-related sequence, an N-terminal partial amino acid sequence composed of a total of 11 amino acid residues, from the position 1 methionine residue to the position 11 alanine residue counting from the N-terminal amino acid residue of the signal peptide sequence with SEQ ID NO: 19.

Sample 39 has, as its APP signal peptide-related sequence, an N-terminal partial amino acid sequence composed of a total of 10 amino acid residues, from the position 1 methionine residue to the position 10 leucine residue counting from the N-terminal amino acid residue of the signal peptide sequence with SEQ ID NO: 19.

Sample 40 has, as its APP signal peptide-related sequence, an N-terminal partial amino acid sequence composed of a total of 9 amino acid residues, from the position 1 methionine residue to the position 9 leucine residue counting from the N-terminal amino acid residue of the signal peptide sequence with SEQ ID NO: 19.

Sample 41 has, as its APP signal peptide-related sequence, an N-terminal partial amino acid sequence composed of a total of 8 amino acid residues, from the position 1 methionine residue to the position 8 leucine residue counting from the N-terminal amino acid residue of the signal peptide sequence with SEQ ID NO: 19.

Sample 42 has, as its APP signal peptide-related sequence, an N-terminal partial amino acid sequence composed of a total of 7 amino acid residues, from the position 1 methionine residue to the position 7 leucine residue counting from the N-terminal amino acid residue of the signal peptide sequence with SEQ ID NO: 19.

In all of these peptides, the carboxyl group (—COOH) of the C-terminal amino acid is amidated (—CONH$_2$). Each of these peptides was synthesized by solid-phase synthesis (Fmoc chemistry) using a commercial peptide synthesizer (an intavis AG system) in accordance with its operation manual. Because the mode of using a peptide synthesizer itself is not distinctive to the present invention, a detailed description is omitted here.

EXAMPLE 5
Evaluation of the Cell Growth-Promoting Activity of the Synthetic Peptides Experimental sections were set up that used the cell growth-promoting peptides obtained in Example 4 (samples 22 to 42) as a cell growth promoter and that used a commercially available bFGF as a cell growth promoter as a comparative example. For the control, a peptide-free section (the bFGF was also not added) was set up.

The details of the evaluation testing are provided below. Each synthesized sample peptide was dissolved in PBS (phosphate-buffered physiological saline) to prepare a stock solution with a peptide concentration of 1 mM.

Rat bone marrow-derived stem cells (mesenchymal stem cells) were used as the test cells. Specifically, the test stem cells were cultured by passage on Dulbecco's MEM medium (DMEM medium: Gibco product) containing 10% fetal bovine serum (FBS: Gibco product), 2 mM of L-glutamine, 50 unit/mL of penicillin, and 50 µg/mL of streptomycin. From the second passage to the fourth passage (passages 2 to 4) were used in this evaluation testing.

Thus, the test stem cells were preliminarily recovered by treatment with a 0.05% trypsin-0.53 mM EDTA solution; a test stem cell solution, prepared with the DMEM medium containing 10 ng/mL of bFGF to provide $1 \times 10^4$ cells/mL, was seeded to each well of a 96-well plate to provide a cell count of $1 \times 10^3$ per well; and pre-cultivation was carried out overnight. The amount of medium was brought to 100 µL per well for this.

The medium in each well was then exchanged for fresh medium to which a stock solution of a peptide selected from sample 22 to 42 had been added, so as to give a concentration of the peptide in each well of approximately 2 µM. For comparison, in some wells the medium in the well was exchanged for fresh medium to which a commercially available bFGF (product of PeproTech) had been added to give a concentration of 10 ng/mL (the bFGF experimental section in Table 6). Wells were also set up that did not contain bFGF or any sample peptide (the control section in Table 6).

After the addition of the sample peptide or bFGF as indicated above, the 96-well plate was placed in a $CO_2$ incubator and cultivation at quiescence was carried out at 37° C. under 5% $CO_2$. Medium exchange was performed every other day. The exchange medium was the same as that used at the start of cultivation (i.e., the same sample peptide or bFGF was also added to the exchange medium as in the sample peptide addition section or bFGF addition section).

During this cultivation test, a "water-soluble tetrazolium salt (WST-8)" was added as a chromogenic reagent to some wells at the start of cultivation (day 0) and at four days after the start of cultivation (day 4). After incubation for 2 hours after the addition, the cell culture fluid to which the chromogenic reagent had been added was recovered. The extent of cell growth was evaluated by a colorimetric method in which, based on reduction of the tetrazolium salt, the absorbance ($OD_{450}$) at a wavelength of 450 nm was measured. The results are represented by Table 6.

TABLE 6

| sample no. | OD450 | |
|---|---|---|
| | at the start of cultivation | after 4 days |
| 22 | 0.051 | 0.241 |
| 23 | 0.051 | 0.391 |
| 24 | 0.051 | 0.327 |
| 25 | 0.051 | 0.319 |
| 26 | 0.051 | 0.509 |
| 27 | 0.051 | 0.511 |
| 28 | 0.051 | 0.532 |
| 29 | 0.051 | 0.434 |
| 30 | 0.051 | 0.413 |
| 31 | 0.051 | 0.401 |
| 32 | 0.051 | 0.433 |
| 33 | 0.051 | 0.407 |
| 34 | 0.051 | 0.243 |
| 35 | 0.051 | 0.299 |
| 36 | 0.051 | 0.288 |
| 37 | 0.051 | 0.571 |
| 38 | 0.051 | 0.491 |
| 39 | 0.051 | 0.538 |
| 40 | 0.051 | 0.487 |
| 41 | 0.051 | 0.311 |
| 42 | 0.051 | 0.346 |
| bFGF | 0.051 | 0.499 |
| control (no addition) | 0.051 | 0.211 |

As is clear from the absorbance values shown in Table 6, the cultivation sections containing the cell growth-promoting peptide disclosed herein (samples 22 to 42) were seen to have an increase in cell growth performance that was the same as for the cultivation section to which bFGF was added. This shows that these sample peptides are peptides that have a very good cell growth-promoting activity.

In particular, when compared to the addition of bFGF, samples 26 to 28, sample 37, and sample 39 had particularly significant cell growth-promoting activities. Normal bone differentiation was seen when the test stem cells grown/produced in these examples were recovered and subjected to a general treatment to induce bone differentiation in this type of stem cell using commercially available materials. This demonstrates that the cell growth-promoting peptide disclosed herein (cell growth promoter) can promote normal cell growth without causing abnormalities (for example, malignant transformation) in the cells subjected for growth.

While the detailed data has not been provided, the same increase in cell growth performance as in these examples was also seen when neural stem cells were used as the subject instead of mesenchymal stem cells as above.

INDUSTRIAL APPLICABILITY

As has been described in the preceding, the cell growth-promoting peptide disclosed herein has a high cell growth-promoting activity and as a result is useful as a substitute for expensive cell growth factors such as bFGF. A cell growth promoter that contains this peptide can be used, for example, as a composition with applications in medical science.

Sequence Listing Free Text

SEQ ID NO: 1 to 62 are synthetic peptides.

The invention claimed is:

1. A method of proliferating mesenchymal stem cells in an undifferentiated state originating from a human or from a non-human mammal, the method comprising:
   preparing an artificially synthesized peptide for promoting proliferation of at least one kind of mesenchymal stem cell in an undifferentiated state; and
   supplying the synthesized peptide at least once to the mesenchymal stem cell subjected to proliferation;
   wherein:
   the artificially synthesized peptide comprises:
   (A) the amino acid sequence consisting of SEQ ID NO: 14, and
   (B) the amino acid sequence consisting of SEQ ID NO: 19, or an N-terminal partial amino acid sequence of SEQ ID NO: 19, or a C-terminal partial amino acid sequence of SEQ ID NO: 19, wherein:
   the N-terminal partial amino acid sequence consists of five or more consecutive amino acid residues counting from the N-terminal amino acid residue of the amino acid sequence of SEQ ID NO: 19, and the C-terminal partial amino acid sequence consists of five or more consecutive amino acid residues counting from the C-terminal amino acid residue of the amino acid sequence of SEQ ID NO: 19.

2. The method according to claim 1, wherein the artificially synthesized peptide comprises the (B) amino acid sequence at the N-terminal side of the (A) amino acid sequence.

3. The method according to claim 1, wherein the synthesized peptide is no more than 40 amino acid residues in length.

4. The method according to claim 1, wherein the artificially synthesized peptide comprises the amino acid sequence consisting of SEQ ID NO: 42.

* * * * *

SEQUENCE LISTING

<160> NUMBER OF SEQ ID NOS: 62

<210> SEQ ID NO 1
<211> LENGTH: 14
<212> TYPE: PRT

-continued

<213> ORGANISM: Artificial sequence
<220> FEATURE:
<223> OTHER INFORMATION: Synthetic peptide

<400> SEQUENCE: 1

Arg Ser Arg Lys Tyr Thr Ser Trp Tyr Val Ala Leu Lys Arg
1               5                   10

<210> SEQ ID NO 2
<211> LENGTH: 19
<212> TYPE: PRT
<213> ORGANISM: Artificial sequence
<220> FEATURE:
<223> OTHER INFORMATION: Synthetic peptide

<400> SEQUENCE: 2

Met Ala Lys Ser Ile Arg Ser Lys His Arg Arg Gln Met Arg Met Met
1               5                   10                  15

Lys Arg Glu

<210> SEQ ID NO 3
<211> LENGTH: 16
<212> TYPE: PRT
<213> ORGANISM: Artificial sequence
<220> FEATURE:
<223> OTHER INFORMATION: Synthetic peptide

<400> SEQUENCE: 3

Met Ala Arg Arg Arg Arg His Arg Gly Pro Arg Arg Pro Arg Pro Pro
1               5                   10                  15

<210> SEQ ID NO 4
<211> LENGTH: 19
<212> TYPE: PRT
<213> ORGANISM: Artificial sequence
<220> FEATURE:
<223> OTHER INFORMATION: Synthetic peptide

<400> SEQUENCE: 4

Gly Arg Cys Arg Arg Leu Ala Asn Phe Gly Pro Arg Lys Arg Arg Arg
1               5                   10                  15

Arg Arg Arg

<210> SEQ ID NO 5
<211> LENGTH: 16
<212> TYPE: PRT
<213> ORGANISM: Artificial sequence
<220> FEATURE:
<223> OTHER INFORMATION: Synthetic peptide

<400> SEQUENCE: 5

Arg Arg Arg Lys Arg Asn Arg Asp Ala Arg Arg Arg Arg Arg Lys Gln
1               5                   10                  15

<210> SEQ ID NO 6
<211> LENGTH: 17
<212> TYPE: PRT
<213> ORGANISM: Artificial sequence
<220> FEATURE:
<223> OTHER INFORMATION: Synthetic peptide

<400> SEQUENCE: 6

Met Gln Arg Lys Pro Thr Ile Arg Arg Lys Asn Leu Arg Leu Arg Arg
1               5                   10                  15

Lys

```
<210> SEQ ID NO 7
<211> LENGTH: 7
<212> TYPE: PRT
<213> ORGANISM: Artificial sequence
<220> FEATURE:
<223> OTHER INFORMATION: Synthetic peptide

<400> SEQUENCE: 7

Ile Met Arg Arg Arg Gly Leu
1               5

<210> SEQ ID NO 8
<211> LENGTH: 8
<212> TYPE: PRT
<213> ORGANISM: Artificial sequence
<220> FEATURE:
<223> OTHER INFORMATION: Synthetic peptide

<400> SEQUENCE: 8

Lys Lys Leu Lys Lys Arg Asn Lys
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic peptide

<400> SEQUENCE: 9

Arg Arg Arg Ala Asn Asn Arg Arg Arg
1               5

<210> SEQ ID NO 10
<211> LENGTH: 7
<212> TYPE: PRT
<213> ORGANISM: Artificial sequence
<220> FEATURE:
<223> OTHER INFORMATION: Synthetic peptide

<400> SEQUENCE: 10

Arg Lys Lys Arg Lys Lys Lys
1               5

<210> SEQ ID NO 11
<211> LENGTH: 15
<212> TYPE: PRT
<213> ORGANISM: Artificial sequence
<220> FEATURE:
<223> OTHER INFORMATION: Synthetic peptide

<400> SEQUENCE: 11

Lys Arg Lys Gly Lys Leu Lys Asn Lys Gly Ser Lys Arg Lys Lys
1               5                   10                  15

<210> SEQ ID NO 12
<211> LENGTH: 18
<212> TYPE: PRT
<213> ORGANISM: Artificial sequence
<220> FEATURE:
<223> OTHER INFORMATION: Synthetic peptide

<400> SEQUENCE: 12

Ser Lys Arg Leu Ser Ser Arg Ala Arg Lys Arg Ala Ala Lys Arg Arg
1               5                   10                  15
```

Leu Gly

```
<210> SEQ ID NO 13
<211> LENGTH: 14
<212> TYPE: PRT
<213> ORGANISM: Artificial sequence
<220> FEATURE:
<223> OTHER INFORMATION: Synthetic peptide

<400> SEQUENCE: 13

Lys Arg Pro Arg Arg Arg Pro Ser Arg Pro Phe Arg Lys Pro
1               5                   10

<210> SEQ ID NO 14
<211> LENGTH: 13
<212> TYPE: PRT
<213> ORGANISM: Artificial sequence
<220> FEATURE:
<223> OTHER INFORMATION: Synthetic peptide

<400> SEQUENCE: 14

Lys Lys Arg Thr Leu Arg Lys Asn Asp Arg Lys Lys Arg
1               5                   10

<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Trp Arg Arg Gln Ala Arg Phe Lys
1               5

<210> SEQ ID NO 16
<211> LENGTH: 11
<212> TYPE: PRT
<213> ORGANISM: Artificial sequence
<220> FEATURE:
<223> OTHER INFORMATION: Synthetic peptide

<400> SEQUENCE: 16

Tyr Gly Arg Lys Lys Arg Arg Gln Arg Arg Arg
1               5                   10

<210> SEQ ID NO 17
<211> LENGTH: 11
<212> TYPE: PRT
<213> ORGANISM: Artificial sequence
<220> FEATURE:
<223> OTHER INFORMATION: Synthetic peptide

<400> SEQUENCE: 17

Tyr Ala Arg Ala Ala Ala Arg Gln Ala Arg Ala
1               5                   10

<210> SEQ ID NO 18
<211> LENGTH: 18
<212> TYPE: PRT
<213> ORGANISM: Artificial sequence
<220> FEATURE:
<223> OTHER INFORMATION: Synthetic peptide

<400> SEQUENCE: 18

Lys Gly Arg Gln Val Lys Val Trp Phe Gln Asn Arg Arg Met Lys Trp
1               5                   10                  15
```

Lys Lys

<210> SEQ ID NO 19
<211> LENGTH: 17
<212> TYPE: PRT
<213> ORGANISM: Artificial sequence
<220> FEATURE:
<223> OTHER INFORMATION: Synthetic peptide

<400> SEQUENCE: 19

Met Leu Pro Gly Leu Ala Leu Leu Leu Ala Ala Trp Thr Ala Arg
1               5                   10                  15

Ala

<210> SEQ ID NO 20
<211> LENGTH: 17
<212> TYPE: PRT
<213> ORGANISM: Artificial sequence
<220> FEATURE:
<223> OTHER INFORMATION: Synthetic peptide

<400> SEQUENCE: 20

Met Leu Pro Ser Leu Ala Leu Leu Leu Ala Ala Trp Thr Val Arg
1               5                   10                  15

Ala

<210> SEQ ID NO 21
<211> LENGTH: 31
<212> TYPE: PRT
<213> ORGANISM: Artificial sequence
<220> FEATURE:
<223> OTHER INFORMATION: Synthetic peptide

<400> SEQUENCE: 21

Met Leu Pro Ser Leu Ala Leu Leu Leu Ala Ala Trp Thr Val Arg
1               5                   10                  15

Ala Gly Lys Lys Arg Thr Leu Arg Lys Asn Asp Arg Lys Lys Arg
            20                  25                  30

<210> SEQ ID NO 22
<211> LENGTH: 29
<212> TYPE: PRT
<213> ORGANISM: Artificial sequence
<220> FEATURE:
<223> OTHER INFORMATION: Synthetic peptide

<400> SEQUENCE: 22

Pro Ser Leu Ala Leu Leu Leu Ala Ala Trp Thr Val Arg Ala Gly
1               5                   10                  15

Lys Lys Arg Thr Leu Arg Lys Asn Asp Arg Lys Lys Arg
            20                  25

<210> SEQ ID NO 23
<211> LENGTH: 28
<212> TYPE: PRT
<213> ORGANISM: Artificial sequence
<220> FEATURE:
<223> OTHER INFORMATION: Synthetic peptide

<400> SEQUENCE: 23

Ser Leu Ala Leu Leu Leu Ala Ala Trp Thr Val Arg Ala Gly Lys
1               5                   10                  15

Lys Arg Thr Leu Arg Lys Asn Asp Arg Lys Lys Arg

```
              20                  25

<210> SEQ ID NO 24
<211> LENGTH: 27
<212> TYPE: PRT
<213> ORGANISM: Artificial sequence
<220> FEATURE:
<223> OTHER INFORMATION: Synthetic peptide

<400> SEQUENCE: 24

Leu Ala Leu Leu Leu Leu Ala Ala Trp Thr Val Arg Ala Gly Lys Lys
1               5                   10                  15

Arg Thr Leu Arg Lys Asn Asp Arg Lys Lys Arg
            20                  25

<210> SEQ ID NO 25
<211> LENGTH: 26
<212> TYPE: PRT
<213> ORGANISM: Artificial sequence
<220> FEATURE:
<223> OTHER INFORMATION: Synthetic peptide

<400> SEQUENCE: 25

Ala Leu Leu Leu Leu Ala Ala Trp Thr Val Arg Ala Gly Lys Lys Arg
1               5                   10                  15

Thr Leu Arg Lys Asn Asp Arg Lys Lys Arg
            20                  25

<210> SEQ ID NO 26
<211> LENGTH: 25
<212> TYPE: PRT
<213> ORGANISM: Artificial sequence
<220> FEATURE:
<223> OTHER INFORMATION: Synthetic peptide

<400> SEQUENCE: 26

Leu Leu Leu Leu Ala Ala Trp Thr Val Arg Ala Gly Lys Lys Arg Thr
1               5                   10                  15

Leu Arg Lys Asn Asp Arg Lys Lys Arg
            20                  25

<210> SEQ ID NO 27
<211> LENGTH: 24
<212> TYPE: PRT
<213> ORGANISM: Artificial sequence
<220> FEATURE:
<223> OTHER INFORMATION: Synthetic peptide

<400> SEQUENCE: 27

Leu Leu Leu Ala Ala Trp Thr Val Arg Ala Gly Lys Lys Arg Thr Leu
1               5                   10                  15

Arg Lys Asn Asp Arg Lys Lys Arg
            20

<210> SEQ ID NO 28
<211> LENGTH: 23
<212> TYPE: PRT
<213> ORGANISM: Artificial sequence
<220> FEATURE:
<223> OTHER INFORMATION: Synthetic peptide

<400> SEQUENCE: 28

Leu Leu Ala Ala Trp Thr Val Arg Ala Gly Lys Lys Arg Thr Leu Arg
1               5                   10                  15
```

Lys Asn Asp Arg Lys Lys Arg
            20

<210> SEQ ID NO 29
<211> LENGTH: 22
<212> TYPE: PRT
<213> ORGANISM: Artificial sequence
<220> FEATURE:
<223> OTHER INFORMATION: Synthetic peptide

<400> SEQUENCE: 29

Leu Ala Ala Trp Thr Val Arg Ala Gly Lys Lys Arg Thr Leu Arg Lys
1               5                   10                  15

Asn Asp Arg Lys Lys Arg
            20

<210> SEQ ID NO 30
<211> LENGTH: 21
<212> TYPE: PRT
<213> ORGANISM: Artificial sequence
<220> FEATURE:
<223> OTHER INFORMATION: Synthetic peptide

<400> SEQUENCE: 30

Ala Ala Trp Thr Val Arg Ala Gly Lys Lys Arg Thr Leu Arg Lys Asn
1               5                   10                  15

Asp Arg Lys Lys Arg
            20

<210> SEQ ID NO 31
<211> LENGTH: 20
<212> TYPE: PRT
<213> ORGANISM: Artificial sequence
<220> FEATURE:
<223> OTHER INFORMATION: Synthetic peptide

<400> SEQUENCE: 31

Ala Trp Thr Val Arg Ala Gly Lys Lys Arg Thr Leu Arg Lys Asn Asp
1               5                   10                  15

Arg Lys Lys Arg
            20

<210> SEQ ID NO 32
<211> LENGTH: 19
<212> TYPE: PRT
<213> ORGANISM: Artificial sequence
<220> FEATURE:
<223> OTHER INFORMATION: Synthetic peptide

<400> SEQUENCE: 32

Trp Thr Val Arg Ala Gly Lys Lys Arg Thr Leu Arg Lys Asn Asp Arg
1               5                   10                  15

Lys Lys Arg

<210> SEQ ID NO 33
<211> LENGTH: 29
<212> TYPE: PRT
<213> ORGANISM: Artificial sequence
<220> FEATURE:
<223> OTHER INFORMATION: Synthetic peptide

<400> SEQUENCE: 33

Met Leu Pro Ser Leu Ala Leu Leu Leu Ala Ala Trp Thr Val Gly
1               5                   10                  15

Lys Lys Arg Thr Leu Arg Lys Asn Asp Arg Lys Lys Arg
            20                  25

<210> SEQ ID NO 34
<211> LENGTH: 28
<212> TYPE: PRT
<213> ORGANISM: Artificial sequence
<220> FEATURE:
<223> OTHER INFORMATION: Synthetic peptide

<400> SEQUENCE: 34

Met Leu Pro Ser Leu Ala Leu Leu Leu Ala Ala Trp Thr Gly Lys
1               5                   10                  15

Lys Arg Thr Leu Arg Lys Asn Asp Arg Lys Lys Arg
            20                  25

<210> SEQ ID NO 35
<211> LENGTH: 27
<212> TYPE: PRT
<213> ORGANISM: Artificial sequence
<220> FEATURE:
<223> OTHER INFORMATION: Synthetic peptide

<400> SEQUENCE: 35

Met Leu Pro Ser Leu Ala Leu Leu Leu Ala Ala Trp Gly Lys Lys
1               5                   10                  15

Arg Thr Leu Arg Lys Asn Asp Arg Lys Lys Arg
            20                  25

<210> SEQ ID NO 36
<211> LENGTH: 26
<212> TYPE: PRT
<213> ORGANISM: Artificial sequence
<220> FEATURE:
<223> OTHER INFORMATION: Synthetic peptide

<400> SEQUENCE: 36

Met Leu Pro Ser Leu Ala Leu Leu Leu Ala Ala Gly Lys Lys Arg
1               5                   10                  15

Thr Leu Arg Lys Asn Asp Arg Lys Lys Arg
            20                  25

<210> SEQ ID NO 37
<211> LENGTH: 25
<212> TYPE: PRT
<213> ORGANISM: Artificial sequence
<220> FEATURE:
<223> OTHER INFORMATION: Synthetic peptide

<400> SEQUENCE: 37

Met Leu Pro Ser Leu Ala Leu Leu Leu Ala Gly Lys Lys Arg Thr
1               5                   10                  15

Leu Arg Lys Asn Asp Arg Lys Lys Arg
            20                  25

<210> SEQ ID NO 38
<211> LENGTH: 24
<212> TYPE: PRT
<213> ORGANISM: Artificial sequence
<220> FEATURE:
<223> OTHER INFORMATION: Synthetic peptide

<400> SEQUENCE: 38

Met Leu Pro Ser Leu Ala Leu Leu Leu Gly Lys Lys Arg Thr Leu
1               5                   10                  15

```
Arg Lys Asn Asp Arg Lys Lys Arg
            20

<210> SEQ ID NO 39
<211> LENGTH: 23
<212> TYPE: PRT
<213> ORGANISM: Artificial sequence
<220> FEATURE:
<223> OTHER INFORMATION: Synthetic peptide

<400> SEQUENCE: 39

Met Leu Pro Ser Leu Ala Leu Leu Leu Gly Lys Lys Arg Thr Leu Arg
1               5                   10                  15

Lys Asn Asp Arg Lys Lys Arg
            20

<210> SEQ ID NO 40
<211> LENGTH: 22
<212> TYPE: PRT
<213> ORGANISM: Artificial sequence
<220> FEATURE:
<223> OTHER INFORMATION: Synthetic peptide

<400> SEQUENCE: 40

Met Leu Pro Ser Leu Ala Leu Leu Gly Lys Lys Arg Thr Leu Arg Lys
1               5                   10                  15

Asn Asp Arg Lys Lys Arg
            20

<210> SEQ ID NO 41
<211> LENGTH: 21
<212> TYPE: PRT
<213> ORGANISM: Artificial sequence
<220> FEATURE:
<223> OTHER INFORMATION: Synthetic peptide

<400> SEQUENCE: 41

Met Leu Pro Ser Leu Ala Leu Gly Lys Lys Arg Thr Leu Arg Lys Asn
1               5                   10                  15

Asp Arg Lys Lys Arg
            20

<210> SEQ ID NO 42
<211> LENGTH: 31
<212> TYPE: PRT
<213> ORGANISM: Artificial sequence
<220> FEATURE:
<223> OTHER INFORMATION: Synthetic peptide

<400> SEQUENCE: 42

Met Leu Pro Gly Leu Ala Leu Leu Leu Ala Ala Trp Thr Ala Arg
1               5                   10                  15

Ala Gly Lys Lys Arg Thr Leu Arg Lys Asn Asp Arg Lys Lys Arg
            20                  25                  30

<210> SEQ ID NO 43
<211> LENGTH: 29
<212> TYPE: PRT
<213> ORGANISM: Artificial sequence
<220> FEATURE:
<223> OTHER INFORMATION: Synthetic peptide

<400> SEQUENCE: 43

Pro Gly Leu Ala Leu Leu Leu Leu Ala Ala Trp Thr Ala Arg Ala Gly
```

```
                1               5                  10                  15
Lys Lys Arg Thr Leu Arg Lys Asn Asp Arg Lys Lys Arg
            20                  25
```

<210> SEQ ID NO 44
<211> LENGTH: 28
<212> TYPE: PRT
<213> ORGANISM: Artificial sequence
<220> FEATURE:
<223> OTHER INFORMATION: Synthetic peptide

<400> SEQUENCE: 44

```
Gly Leu Ala Leu Leu Leu Ala Ala Trp Thr Ala Arg Ala Gly Lys
1               5                  10                  15
Lys Arg Thr Leu Arg Lys Asn Asp Arg Lys Lys Arg
            20                  25
```

<210> SEQ ID NO 45
<211> LENGTH: 27
<212> TYPE: PRT
<213> ORGANISM: Artificial sequence
<220> FEATURE:
<223> OTHER INFORMATION: Synthetic peptide

<400> SEQUENCE: 45

```
Leu Ala Leu Leu Leu Ala Ala Trp Thr Ala Arg Ala Gly Lys Lys
1               5                  10                  15
Arg Thr Leu Arg Lys Asn Asp Arg Lys Lys Arg
            20                  25
```

<210> SEQ ID NO 46
<211> LENGTH: 26
<212> TYPE: PRT
<213> ORGANISM: Artificial sequence
<220> FEATURE:
<223> OTHER INFORMATION: Synthetic peptide

<400> SEQUENCE: 46

```
Ala Leu Leu Leu Ala Ala Trp Thr Ala Arg Ala Gly Lys Lys Arg
1               5                  10                  15
Thr Leu Arg Lys Asn Asp Arg Lys Lys Arg
            20                  25
```

<210> SEQ ID NO 47
<211> LENGTH: 25
<212> TYPE: PRT
<213> ORGANISM: Artificial sequence
<220> FEATURE:
<223> OTHER INFORMATION: Synthetic peptide

<400> SEQUENCE: 47

```
Leu Leu Leu Leu Ala Ala Trp Thr Ala Arg Ala Gly Lys Lys Arg Thr
1               5                  10                  15
Leu Arg Lys Asn Asp Arg Lys Lys Arg
            20                  25
```

<210> SEQ ID NO 48
<211> LENGTH: 24
<212> TYPE: PRT
<213> ORGANISM: Artificial sequence
<220> FEATURE:
<223> OTHER INFORMATION: Synthetic peptide

<400> SEQUENCE: 48

-continued

Leu Leu Leu Ala Ala Trp Thr Ala Arg Ala Gly Lys Lys Arg Thr Leu
1               5                   10                  15

Arg Lys Asn Asp Arg Lys Lys Arg
            20

<210> SEQ ID NO 49
<211> LENGTH: 23
<212> TYPE: PRT
<213> ORGANISM: Artificial sequence
<220> FEATURE:
<223> OTHER INFORMATION: Synthetic peptide

<400> SEQUENCE: 49

Leu Leu Ala Ala Trp Thr Ala Arg Ala Gly Lys Lys Arg Thr Leu Arg
1               5                   10                  15

Lys Asn Asp Arg Lys Lys Arg
            20

<210> SEQ ID NO 50
<211> LENGTH: 22
<212> TYPE: PRT
<213> ORGANISM: Artificial sequence
<220> FEATURE:
<223> OTHER INFORMATION: Synthetic peptide

<400> SEQUENCE: 50

Leu Ala Ala Trp Thr Ala Arg Ala Gly Lys Lys Arg Thr Leu Arg Lys
1               5                   10                  15

Asn Asp Arg Lys Lys Arg
            20

<210> SEQ ID NO 51
<211> LENGTH: 21
<212> TYPE: PRT
<213> ORGANISM: Artificial sequence
<220> FEATURE:
<223> OTHER INFORMATION: Synthetic peptide

<400> SEQUENCE: 51

Ala Ala Trp Thr Ala Arg Ala Gly Lys Lys Arg Thr Leu Arg Lys Asn
1               5                   10                  15

Asp Arg Lys Lys Arg
            20

<210> SEQ ID NO 52
<211> LENGTH: 20
<212> TYPE: PRT
<213> ORGANISM: Artificial sequence
<220> FEATURE:
<223> OTHER INFORMATION: Synthetic peptide

<400> SEQUENCE: 52

Ala Trp Thr Ala Arg Ala Gly Lys Lys Arg Thr Leu Arg Lys Asn Asp
1               5                   10                  15

Arg Lys Lys Arg
            20

<210> SEQ ID NO 53
<211> LENGTH: 19
<212> TYPE: PRT
<213> ORGANISM: Artificial sequence
<220> FEATURE:
<223> OTHER INFORMATION: Synthetic peptide

<400> SEQUENCE: 53

Trp Thr Ala Arg Ala Gly Lys Lys Arg Thr Leu Arg Lys Asn Asp Arg
1               5                   10                  15

Lys Lys Arg

<210> SEQ ID NO 54
<211> LENGTH: 29
<212> TYPE: PRT
<213> ORGANISM: Artificial sequence
<220> FEATURE:
<223> OTHER INFORMATION: Synthetic peptide

<400> SEQUENCE: 54

Met Leu Pro Gly Leu Ala Leu Leu Leu Ala Ala Trp Thr Ala Gly
1               5                   10                  15

Lys Lys Arg Thr Leu Arg Lys Asn Asp Arg Lys Lys Arg
            20                  25

<210> SEQ ID NO 55
<211> LENGTH: 28
<212> TYPE: PRT
<213> ORGANISM: Artificial sequence
<220> FEATURE:
<223> OTHER INFORMATION: Synthetic peptide

<400> SEQUENCE: 55

Met Leu Pro Gly Leu Ala Leu Leu Leu Ala Ala Trp Thr Gly Lys
1               5                   10                  15

Lys Arg Thr Leu Arg Lys Asn Asp Arg Lys Lys Arg
            20                  25

<210> SEQ ID NO 56
<211> LENGTH: 27
<212> TYPE: PRT
<213> ORGANISM: Artificial sequence
<220> FEATURE:
<223> OTHER INFORMATION: Synthetic peptide

<400> SEQUENCE: 56

Met Leu Pro Gly Leu Ala Leu Leu Leu Ala Ala Trp Gly Lys Lys
1               5                   10                  15

Arg Thr Leu Arg Lys Asn Asp Arg Lys Lys Arg
            20                  25

<210> SEQ ID NO 57
<211> LENGTH: 26
<212> TYPE: PRT
<213> ORGANISM: Artificial sequence
<220> FEATURE:
<223> OTHER INFORMATION: Synthetic peptide

<400> SEQUENCE: 57

Met Leu Pro Gly Leu Ala Leu Leu Leu Ala Ala Gly Lys Lys Arg
1               5                   10                  15

Thr Leu Arg Lys Asn Asp Arg Lys Lys Arg
            20                  25

<210> SEQ ID NO 58
<211> LENGTH: 25
<212> TYPE: PRT
<213> ORGANISM: Artificial sequence
<220> FEATURE:
<223> OTHER INFORMATION: Synthetic peptide

<400> SEQUENCE: 58

Met Leu Pro Gly Leu Ala Leu Leu Leu Ala Gly Lys Lys Arg Thr
1               5                   10                  15

Leu Arg Lys Asn Asp Arg Lys Lys Arg
            20                  25

<210> SEQ ID NO 59
<211> LENGTH: 24
<212> TYPE: PRT
<213> ORGANISM: Artificial sequence
<220> FEATURE:
<223> OTHER INFORMATION: Synthetic peptide

<400> SEQUENCE: 59

Met Leu Pro Gly Leu Ala Leu Leu Leu Gly Lys Lys Arg Thr Leu
1               5                   10                  15

Arg Lys Asn Asp Arg Lys Lys Arg
            20

<210> SEQ ID NO 60
<211> LENGTH: 23
<212> TYPE: PRT
<213> ORGANISM: Artificial sequence
<220> FEATURE:
<223> OTHER INFORMATION: Synthetic peptide

<400> SEQUENCE: 60

Met Leu Pro Gly Leu Ala Leu Leu Gly Lys Lys Arg Thr Leu Arg
1               5                   10                  15

Lys Asn Asp Arg Lys Lys Arg
            20

<210> SEQ ID NO 61
<211> LENGTH: 22
<212> TYPE: PRT
<213> ORGANISM: Artificial sequence
<220> FEATURE:
<223> OTHER INFORMATION: Synthetic peptide

<400> SEQUENCE: 61

Met Leu Pro Gly Leu Ala Leu Gly Lys Lys Arg Thr Leu Arg Lys
1               5                   10                  15

Asn Asp Arg Lys Lys Arg
            20

<210> SEQ ID NO 62
<211> LENGTH: 21
<212> TYPE: PRT
<213> ORGANISM: Artificial sequence
<220> FEATURE:
<223> OTHER INFORMATION: Synthetic peptide

<400> SEQUENCE: 62

Met Leu Pro Gly Leu Ala Leu Gly Lys Lys Arg Thr Leu Arg Lys Asn
1               5                   10                  15

Asp Arg Lys Lys Arg
            20